United States Patent
Boxer et al.

(10) Patent No.: US 9,447,087 B2
(45) Date of Patent: Sep. 20, 2016

(54) GALACTOKINASE INHIBITORS FOR THE TREATMENT AND PREVENTION OF ASSOCIATED DISEASES AND DISORDERS

(75) Inventors: Matthew B. Boxer, New Market, MD (US); Martin J. Walsh, Carmel, IN (US); Li Liu, Germantown, MD (US); Cordelle D. Tanega, Virginia Beach, VA (US); Min Shen, Boyds, MD (US); Kent Lai, Salt Lake City, UT (US); Manshu Tang, Salt Lake City, UT (US); Douglas S. Auld, Beverly, MA (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 14/346,400

(22) PCT Filed: Sep. 23, 2011

(86) PCT No.: PCT/US2011/053021
§ 371 (c)(1),
(2), (4) Date: Jun. 9, 2014

(87) PCT Pub. No.: WO2013/043192
PCT Pub. Date: Mar. 28, 2013

(65) Prior Publication Data
US 2014/0288100 A1     Sep. 25, 2014

(51) Int. Cl.
| | |
|---|---|
| C07D 403/12 | (2006.01) |
| A61K 31/506 | (2006.01) |
| C07D 417/14 | (2006.01) |
| C07D 413/14 | (2006.01) |
| C07D 413/12 | (2006.01) |
| C07D 493/10 | (2006.01) |
| C07D 495/10 | (2006.01) |
| C07D 491/107 | (2006.01) |

(52) U.S. Cl.
CPC ........... C07D 417/14 (2013.01); A61K 31/506 (2013.01); C07D 403/12 (2013.01); C07D 413/12 (2013.01); C07D 413/14 (2013.01); C07D 491/107 (2013.01); C07D 493/10 (2013.01); C07D 495/10 (2013.01)

(58) Field of Classification Search
CPC .......................... C07D 403/12; A61K 31/506
USPC ........................................... 544/331; 514/275
See application file for complete search history.

(56) References Cited

FOREIGN PATENT DOCUMENTS

WO   WO 2009/023773 A2   2/2009
WO   WO 2009/023773 A3   2/2009

OTHER PUBLICATIONS

AKos Consulting and Solutions GmbH (Registry, STN Files: Chemcats), pp. 3-22 (Jan. 2005).*
Baselga, Targeting Tyrosine Kinases in Cancer: The Second Wave, Science, vol. 312, pp. 1175-1178 (May 2006).*
Chemical Block Ltd. (Registry, STN Files: Chemcats) (Aug. 2004).*
Fridovich-Keil, Galactosemia: The Good, the Bad, and the Unknown, Journal of Cellular Physiology, 209, pp. 701-705 (2006).*
Galactosemia, Natural Living Center, 5 pages (2011).*
Goldfarb, CAPLUS Abstract 151:92851 (2009).*
Gura et al., Systems for identifying new drugs are often faulty, Science, 278:1041-1042, 1997.*
Holden et al., Galactokinase: structure, function and role in type II galactosemia, CMLS, Cell Mol. Life Sci., 61, pp. 2471-2484 (2004).*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Scientific Exchange, Inc. (Registry, STN Files: Chemcats), pp. 23-26, 28-36, 38-43 (Nov. 2004).*
Simone, Oncology: Introduction, Cecil Textbook of Medicine, 20th Edition, vol. 1, pp. 1004-1101 O, 1995.*
Vitas-M (Registry, STN Files: Chemcats) p. 27 and 37 (Nov. 2004).*
Boxer et al., "Toward Improved Therapy for Classic Galactosemia," *Probe Reports from the NIH Molecular Libraries Program*, 1-19 (2011).
Database Registry Chemical Accession No. 669718-43-8, "5(1H)-Quinazolinone, 2-(2-benzothiazolylamino)-4,6,7,8-tetrahydro-4-phenyl-," (Apr. 1, 2004).
Database Registry Chemical Accession No. 669718-44-9, "5(1H)-Quinazolinone, 2-(2-benzothiazolylamino)-4,6,7,8-tetrahydro-4-(4-methylphenyl)-," (Apr. 1, 2004).

(Continued)

*Primary Examiner* — Deepak Rao
(74) *Attorney, Agent, or Firm* — Stoel Rives LLP

(57) ABSTRACT

Disclosed are inhibitors of human galactokinase of formula (1) that are useful in treating or preventing a galactokinase mediated disease or disorder, e.g., galactosemia. Also disclosed are a composition comprising a pharmaceutically acceptable carrier and at least one inhibitor of the invention, and a method of treating or preventing such disease or disorder in a mammal. Formula (I).

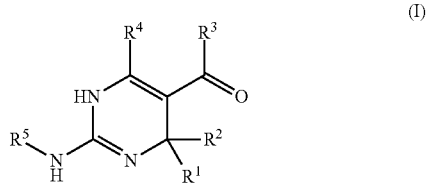

13 Claims, No Drawings

(56) References Cited

OTHER PUBLICATIONS

Database Registry Chemical Accession No. 727686-84-2, "5-Pyrimidinecarboxamide, 2-(2-benzoxazolylamino)-4-(4-fluorophenyl)-1,4-dihydro-6-methyl-N-phenyl-," (Aug. 17, 2004).

Database Registry Chemical Accession No. 777868-32-3, "5(1H)-Quinazolinone, 2-(2-benzoxazolylamino)-4,6,7,8-tetrahydro-7,7-dimethyl-4-(4-pyridinyl)-," (Nov. 10, 2004).

Database Registry Chemical Accession No. 810635-65-5, "Spiro[piperidine-4,4'(3'H)- quinazolin]-5'(6'H)-one, 2'-(2-benzoxazolylamino)-7',8'-dihydro-1,7',7'-trimethyl-," (Jan. 9, 2005).

Odejinmi et al., "Structure-Activity Analysis and Cell-Based Optimization of Human Galactokinase Inhibitors," *ACS Med. Chem. Lett.*, 2(9), 667-672 (2011).

Potapov et al., "Three-Component Condensation of Hetarylguanidines with Aldehydes (Ketones) and Dicarbonyl Compounds," *Chem. Heterocycl. Comp.*, 42 (10), 1338-1342 (2006).

PubChem Compound NCGC00188570-01, retrieved from the Internet: URL:http://pubchem.ncbi.nlm.nih.gov/summary/summary.cgi?sid=87550835&viewopt=PubChem [retrieved on Jun. 25, 2012] (Mar. 10, 2010).

\* cited by examiner

GALACTOKINASE INHIBITORS FOR THE TREATMENT AND PREVENTION OF ASSOCIATED DISEASES AND DISORDERS

CROSS-REFERENCE TO A RELATED APPLICATION

This patent application is a U.S. National Phase of International Patent Application No. PCT/US11/53021, filed Sep. 23, 2011, which is incorporated by reference.

BACKGROUND OF THE INVENTION

Galactose is an abundant hexose existing as lactose in milk, dairy products, fruits, vegetables and many other foods (Acosta, P. B. and K. C. Gross, *Eur. J. Pediatr,* 1995. 154(7 Suppl. 2): p. S87-92; Berry, G. T., et al., *J. Inherit. Metab. Dis,* 1993. 16(1): p. 91-100). It is metabolized through an evolutionarily conserved pathway referred to as the Leloir pathway (Leloir, L. F., *Arch Biochem,* 1951. 33(2): p. 186-90). The first enzyme of the pathway, galactokinase (GALK), converts α-D-galactose to galactose-1-phosphate (gal-1-p) (Atkinson, M. R., E. Johnson, and R. K. Morton, *Nature,* 1959. 184: p. 1925-7). Then, in the presence of the second enzyme, galactose-1-phosphate uridyltransferase (GALT), gal-1-P will react with UDP-glucose to form UDP-galactose and glucose-1-phosphate (Arabshahi, A., et al., *Biochemistry,* 1986. 25(19): p. 5583-9).

Deficiency of GALT results in a potentially lethal disorder called Classic Galactosemia (CG) (Isselbacher, K. J., et al., *Science,* 1956. 123(3198): p. 635-6; Rennert, O. M., *Annals of clinical and laboratory science,* 1977. 7(6): p. 443-8). Patients with CG accumulate high level of gal-1-p which can result in severe disease during the newborn period, including liver failure, coagulopathy, coma, and death if not treated (Goppert, F., *Klin. Wschr.,* 1917(54): p. 473-477; Mason H, T. M., *Am. J. Dis. Child.,* 1935(50): p. 359-374; Tyfield, L., et al., *Hum. Mutat.,* 1999. 13(6): p. 417-30). Although removal of galactose from the diet can prevent neonatal death, CG patients still develop chronic complications such as premature ovarian insufficiency (POI), ataxia, speech dyspraxia and mental retardation even in galactose-restricted diet (Waggoner, D., Buist, N R M, Donnell, G N, *Journal of Inherited Metabolic Disorders,* 1990. 13: p. 802-818; Waggoner, D., Buist, N R M, *International Pediatrics,* 1993. 8: p. 97-100).

The mechanisms for the above chronic complications remain uncertain, but several lines of evidences indicate accumulation of gal-1-p is a major factor that contributes to these complications. Except for cataracts, patients with an inherited deficiency of GALK do not experience the complications observed in GALT-deficient patients (Gitzelmann, R., H. J. Wells, and S. Segal, *Eur. J. Clin. Invest.,* 1974. 4(2): p. 79-84; Gitzelmann, R., *J. Pediatr.,* 1975. 87(6 Pt 1): p. 1007-8). Similarly, while gal7 (i.e., GALT-deficient) mutant yeast stops growing upon galactose challenge, a gal 7 gal1 double mutant strain (i.e., GALT- and GALK-deficient) is no longer sensitive to galactose (Douglas, H. C. and D. C. Hawthorne, *Genetics,* 1964. 49: p. 837-44; Douglas, H. C. and D. C. Hawthorne, *Genetics,* 1966. 54(3): p. 911-6). A significant amount of galactose is found in non-dairy foods such as vegetables and fruits, and more importantly, galactose is also produced endogenously from the natural turnover of glycolipids and glycoproteins. Moreover, using isotope labeling, Berry et al. demonstrated that a 50 kg adult male could produce up to 2 grams of galactose per day (Berry, G. T., et al., *Mol. Genet. Metab.,* 2004. 81(1): p. 22-30; Berry, G. T., et al., *Eur. J. Pediatr.,* 1997. 156 Suppl. 1: p. S43-9; Berry, G. T., et al., *Lancet,* 1995. 346(8982): p. 1073-4).

In addition, it is known that GALKmodifies the PTEN/AKT pathway in a number of human tissues and human cell lines. The galactose-1-phosphate produced by GALK feeds into glycolysis. GALK1 is over-expressed in a number of tumors. Thus, inhibition of GALK may down regulate the PTEN/ATK pathway and therefore interfere with tumor growth and/or development.

The foregoing shows that there is an unmet need for inhibitors of galactokinase enzyme and agents for the prophylaxis and/or therapy of diseases preventable or treatable by inhibiting the enzyme.

BRIEF SUMMARY OF THE INVENTION

The invention provides galactokinase inhibitors, e.g., a compound of formula (I):

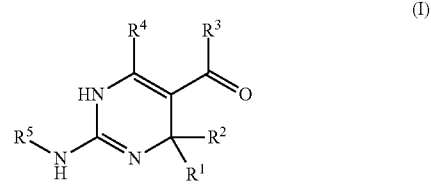

wherein $R^1$ and $R^2$ are each independently selected from the group consisting of hydrogen, alkyl, aryl, and heteroaryl or wherein $R^1$ and $R^2$, taken together along with the carbon atoms to which they are attached, form a 5- to 7-membered carbocyclic or heterocyclic ring, wherein $R^3$ is selected from the group consisting of —NH-alkyl, —NH-cycloalkyl, —NH-aryl, —NH-alkylaryl, —NH-heteroaryl, —N-heteroaryl, and —NR$^{12}$R$^{13}$ wherein $R^{12}$ and $R^{13}$ are each independently selected from the group consisting of hydrogen, alkyl, cycloalkyl, aryl, arylalkyl, and heteroaryl, or wherein $R^{12}$ and $R^{13}$ together form a heteroaryl or a heterocycloalkyl, wherein $R^4$ is selected from the group consisting of hydrogen and alkyl, or wherein $R^3$ and $R^4$ together form a group of the formula:

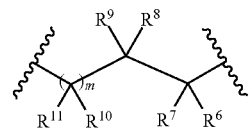

wherein $R^6$, $R^7$, $R^8$, $R^9$, $R^{10}$, and $R^{11}$ are each independently selected from the group consisting of hydrogen, alkyl, aryl, and heteroaryl, wherein m is 0 or 1, wherein $R^5$ is heteroaryl, wherein alkyl, aryl, heterocycloalkyl, carbocyclic ring, heterocyclic ring, arylalkyl, and heteroaryl groups are unsubstituted or optionally substituted with one or more substituents selected from the group consisting of alkyl, aryl, halo, trifluoromethyl, alkoxy, aryloxy, amino, alkylamino, and dialkylamino, or a pharmaceutically acceptable salt thereof.

The invention also provides a pharmaceutical composition comprising a compound or salt of the invention and a pharmaceutically acceptable carrier.

The invention further provides method for treating or preventing a human galactokinase mediated disease or disorder in a mammal, comprising administering to the mammal in need thereof, a therapeutically or prophylactically effective amount of a compound of the invention or salt thereof.

The invention additionally provides a method for treating or preventing a PTEN/AKT mis-regulated cancer in a mammal, comprising administering to the mammal in need of, a therapeutically or prophylactically effective amount of a compound of the invention, salt thereof, enantiomers thereof, a mixture of enantiomers thereof, or diastereomers thereof of a compound.

The invention further provides a method of reducing the level of galactose-1-phosphate in a cell, comprising contacting the cell with effective amount of a compound of the invention, salt thereof, enantiomers thereof, a mixture of enantiomers thereof, or diastereomers thereof.

DETAILED DESCRIPTION OF THE INVENTION

In accordance with an embodiment, the invention provides a compound of formula (I):

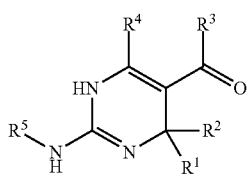

(I)

wherein $R^1$ and $R^2$ are each independently selected from the group consisting of hydrogen, alkyl, aryl, and heretoaryl or wherein $R^1$ and $R^2$, taken together along with the carbon atoms to which they are attached, form a 5- to 7-membered carbocyclic or heterocyclic ring, wherein $R^3$ is selected from the group consisting of —NH-alkyl, —NH-cycloalkyl, —NH-aryl, —NH-alkylaryl, —NH-heteroaryl, —N-heteroaryl, and —NR$^{12}$R$^{13}$ wherein $R^{12}$ and $R^{13}$ are each independently selected from the group consisting of hydrogen, alkyl, cycloalkyl, aryl, arylalkyl, and heteroaryl, or wherein $R^{12}$ and $R^{13}$ together form a heteroaryl or a heterocycloalkyl, wherein $R^4$ is selected from the group consisting of hydrogen and alkyl, or wherein $R^3$ and $R^4$ together form a group of the formula:

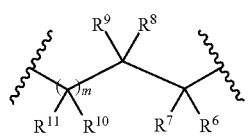

wherein $R^6$, $R^7$, $R^8$, $R^9$, $R^{10}$, and $R^{11}$ are each independently selected from the group consisting of hydrogen, alkyl, aryl, and heteroaryl, wherein m is 0 or 1, wherein $R^5$ is heteroaryl, wherein alkyl, aryl, heterocycloalkyl, carbocyclic ring, heterocyclic ring, arylalkyl, and heteroaryl groups are unsubstituted or optionally substituted with one or more substituents selected from the group consisting of alkyl, aryl, halo, trifluoromethyl, alkoxy, aryloxy, amino, alkylamino, and dialkylamino, with the proviso that when $R^5$ is benzoxazol-2-yl, $R^1$ is hydrogen, $R^2$ is phenyl, $R^3$ and $R^4$ together form

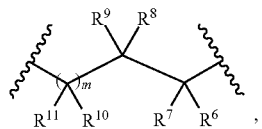

and m is 1, $R^{10}$ and $R^{11}$ are not simultaneously methyl, or a pharmaceutically acceptable salt thereof.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "cycloalkyl," as used herein, means a cyclic alkyl substituent containing from, for example, about 3 to about 8 carbon atoms, preferably from about 43 to about 7 carbon atoms, and more preferably from about 5 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with one or more alkyl groups such as methyl groups, ethyl groups, and the like.

The term "heteroaryl," as used herein, refers to a 5, 6, or 7-membered aromatic ring system containing one or more heteroatoms selected from the group consisting of O, N, S, and combinations thereof. The heteroaryl group can be any suitable heteroaryl group. The heteroaryl group can be a monocyclic heteroaryl group or a bicyclic heteroaryl group. Suitable bicyclic heteroaryl groups include monocylic heteroaryl rings fused to a $C_6$-$C_{10}$ aryl ring. It is understood that a 6-membered heteroaryl group comprises $4n+2\pi$ electrons, according to Hückel's Rule, and that a 5-, 7-, and 8-membered heteroaryl group has six electrons provided from a combination of p orbitals and an unshared pair of electrons provided by a heteroatom or heteroatoms which occupy bonding orbitals and constitute an aromatic sextet. Non-limiting examples of suitable heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, and quinazolinyl. The heteroaryl group can be linked at any open position of the heteroaryl group. For example, the furanyl group can be a furan-2-yl group or a furan-3-yl group, and the thiophenyl group can be a thiophene-2-yl group or a thiophene-3-yl group. The heteroaryl group is optionally substituted with 1, 2, 3, 4, or 5 substituents as recited herein, wherein the optional substituent can be present at any open position on the heterocyclyl group.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2π electrons, according to Hückel's Rule.

The term "alkylaryl" refers to an unsubstituted or substituted alkyl group bonded to an unsubstituted or substituted aryl group. The alkylaryl group is typically bonded to the core structure of the molecule by way of the alkyl portion of the alkylaryl group.

The term "heterocycloalkyl," as used herein, means a non-aromatic cyclic alkyl substituent containing a heteroatom and further containing from, for example, about 3 to about 7 carbon atoms, preferably from about 3 to about 6 carbon atoms, and more preferably from about 3 to about 5 carbon atoms. The heterocycloalkyl group can be monocyclic or can be fused to another ring, wherein the other ring can be a cycloalkyl ring, an aryl ring, or another heterocycloalkyl ring. Examples of such substituents include tetrahydrofuranyl, tetrahydrothiophenyl, pyrrolidinyl, piperidinyl, tetrahydroazepinyl, and the like. The heterocycloalkyl groups may be unsubstituted or further substituted with alkyl groups such as methyl groups, ethyl groups, and the like.

In certain embodiments of the compound of formula (I), $R^5$ is selected from the group consisting of benzoxazol-2-yl, 5-bromo-benzoxazol-2-yl, 5-methyl-benzoxazol-2-yl, 6-methyl-benzoxazol-2-yl, 6-phenyl-benzoxazol-2-yl, benzoimidazol-2-yl, benzothiazol-2-yl, indol-1-yl, indol-2-yl, indol-3-yl, furan-2-yl, furan-3-yl, thiophene-2-yl, thiophene-3-yl, imidazol-1-yl, imidazol-4-yl, thiazol-2-yl, thiazol-4-yl, pyrazol-3-yl, pyrazol-4-yl, pyridin-2-yl, pyridin-3-yl, and pyridin-4-yl.

In preferred embodiments, $R^5$ is selected from the group consisting of benzoxazol-2-yl, 5-bromo-benzoxazol-2-yl, 5-methyl-benzoxazol-2-yl, 6-methyl-benzoxazol-2-yl, and 6-phenyl-benzoxazol-2-yl.

In a more preferred embodiment, $R^5$ is benzoxazol-2-yl.

In accordance with an embodiment, $R^3$ and $R^4$ together form

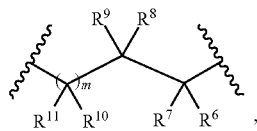

wherein m is 1, and wherein the compound has the formula (Ia):

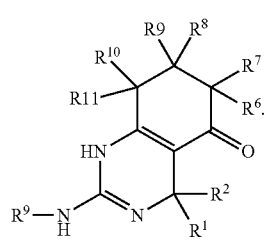

In accordance with another embodiment of the compound of formula (Ia), $R^1$ is hydrogen and $R^2$ is phenyl optionally substituted with one or more substituents selected from the group consisting of halogen, trifluoromethyl, alkyl, alkoxy, aryloxy, and dialkylamino.

In accordance with another embodiment of the compound of formula (Ia), $R^1$ is hydrogen and $R^2$ is heteroaryl optionally substituted with one or more substituents selected from the group consisting of halogen, trifluoromethyl, alkyl, alkoxy, aryloxy, and dialkylamino.

In accordance with an embodiment, specific examples of the formula (Ia) include those wherein $R^6$, $R^7$, $R^{10}$, and $R^{11}$ are hydrogen.

In accordance with another embodiment, specific examples of the formula (Ia) include those wherein $R^8$ and $R^9$ are both hydrogen.

In accordance with another embodiment, specific examples of the formula (Ia) include those wherein $R^8$ and $R^9$ are both methyl.

In accordance with another embodiment, specific examples of the formula (Ia) include those wherein $R^8$ is hydrogen and $R^9$ is hydrogen or phenyl optionally substituted with one or more substituents selected from the group consisting of halo, trifluoromethyl, alkyl, alkoxy, aryloxy, amino, alkylamino, and dialkylamino, or heteroaryl optionally substituted with one or more substituents selected from the group consisting of halo, trifluoromethyl, alkyl, alkoxy, aryloxy, amino, alkylamino, and dialkylamino.

In accordance with preferred embodiments, specific examples of the formula (Ia) include those wherein $R^9$ is phenyl substituted with one or more substituents selected from the group consisting of halo, trifluoromethyl, alkyl, alkoxy, and dialkylamino.

In accordance with other preferred embodiments, specific examples of the formula (Ia) include those wherein $R^9$ is heteroaryl selected from the group consisting of 5-methylthiophen-2-yl, pyridine-3-yl, pyridine-4-yl, 2-chloropyridin-4-yl, 3-trifluoropyridin-2-yl, 4-trifluoromethylpyridin-3-yl, 2-chloropyridin-3-yl, 2-bromopyridin-3-yl, 3-methylthophen-2-yl, 3-bromopyridin-4-yl, 4-bromopyrazol-3-yl, 4-bromo-1-methylpyrazol-3-yl, 3-bromopyridin-4-yl, 4-chloro-1-methylpyrazol-3-yl, pyrazol-3-yl, 5-methylpyrazol-3-yl, and 4-chloro-1-methylpyrazol-3-yl.

In keeping with the embodiments described above, specific examples of compounds include compounds selected from the group consisting of:

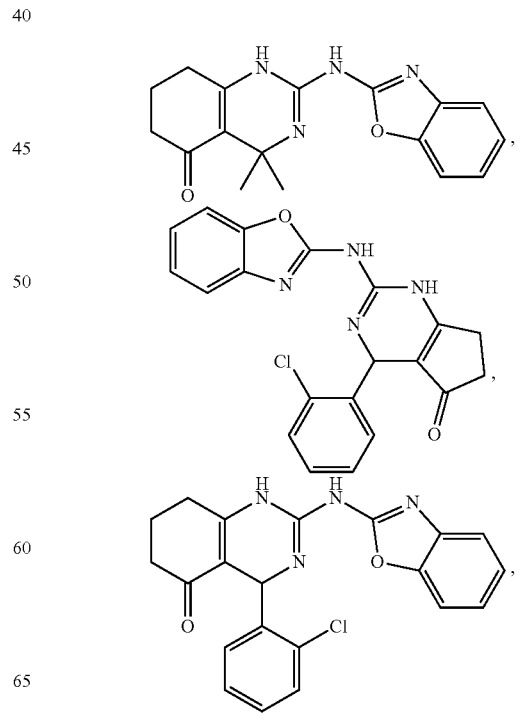

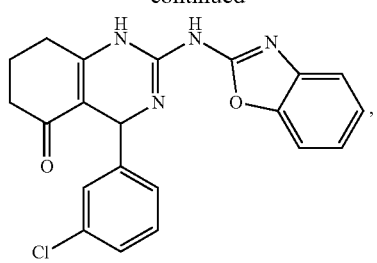,
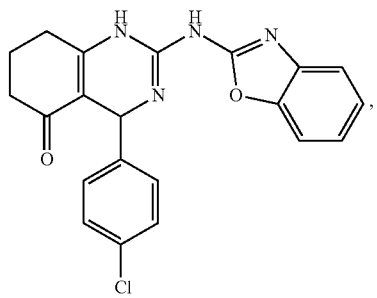,
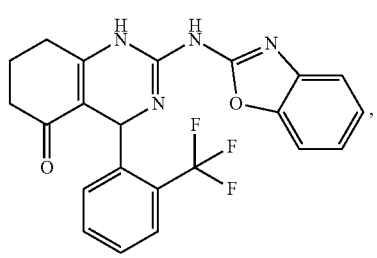,
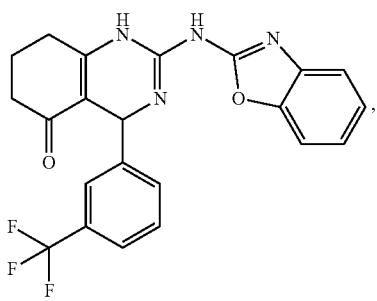,
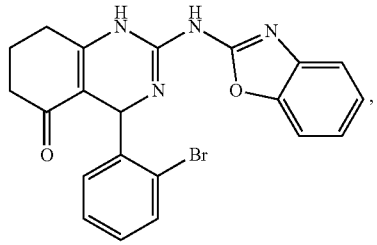,
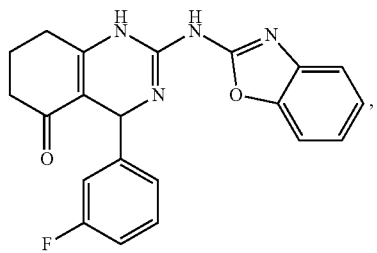,
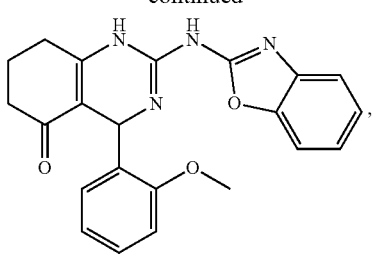,
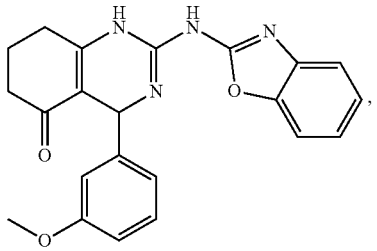,
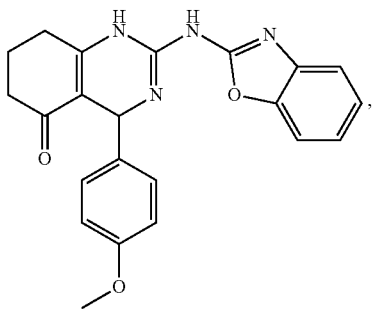,
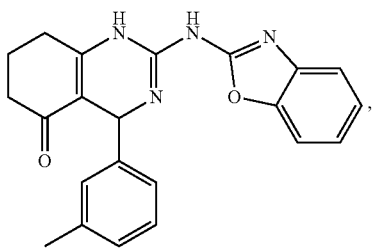,
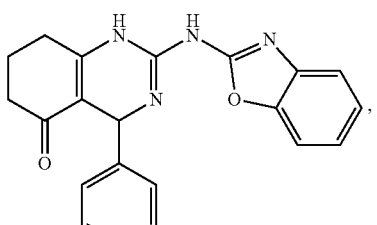,
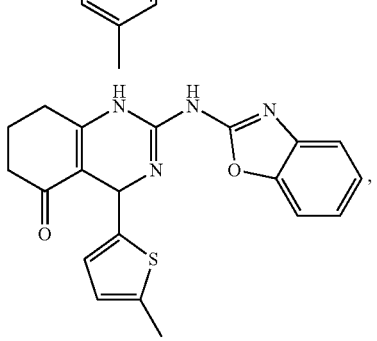,

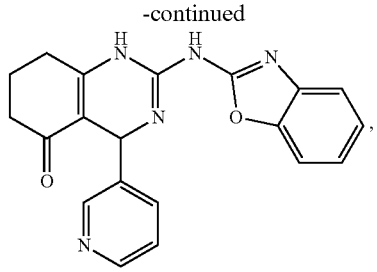,
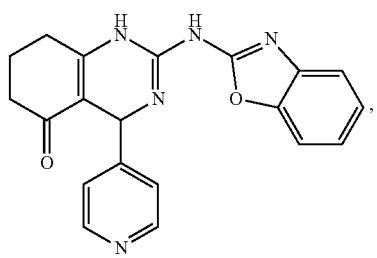,
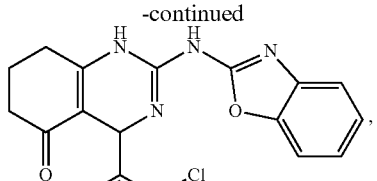,
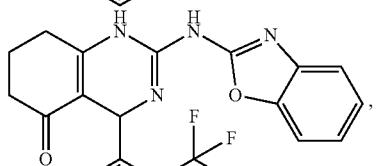,
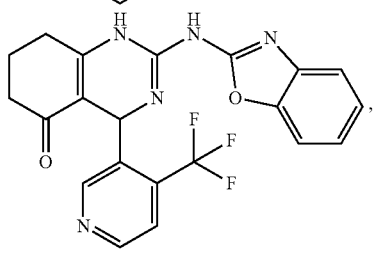,
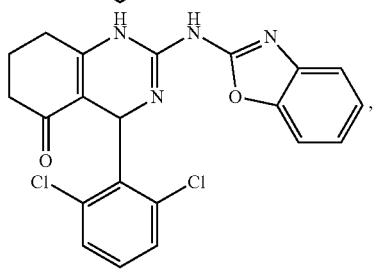,
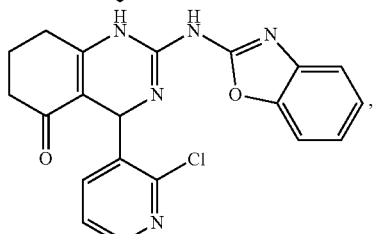,
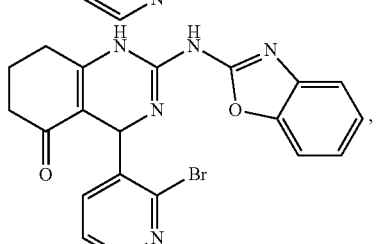,
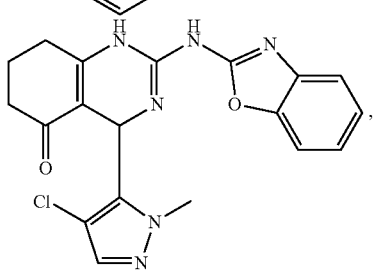,

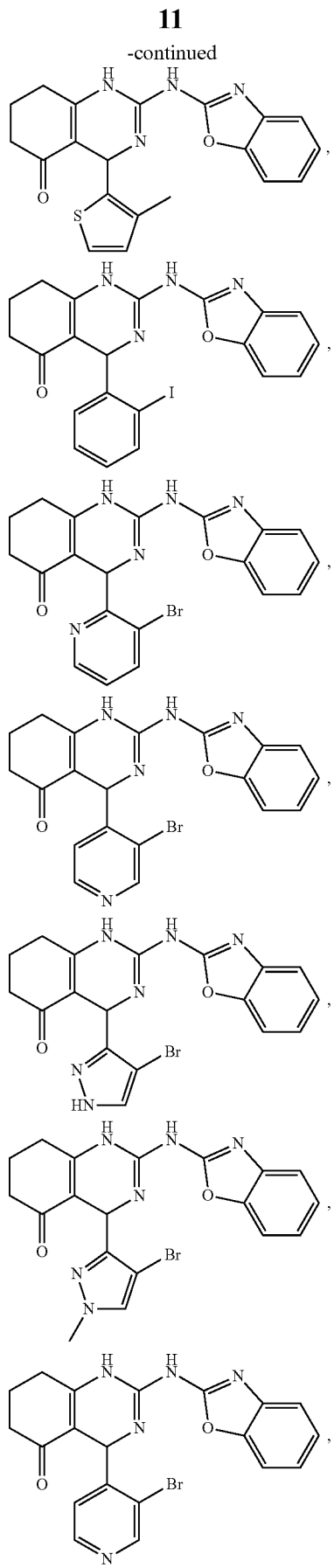

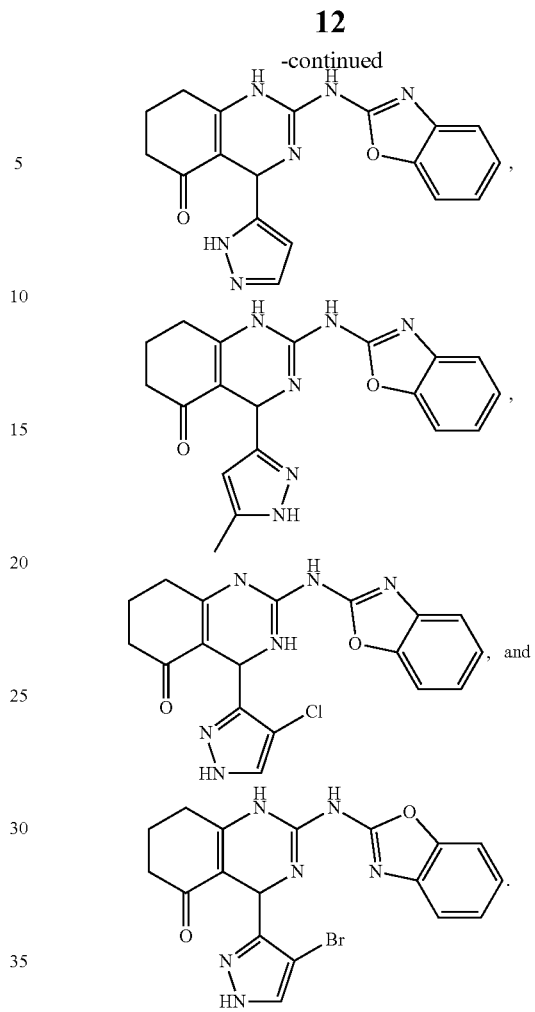

In accordance with an embodiment, the compound of formula (I) has the formula (Ib):

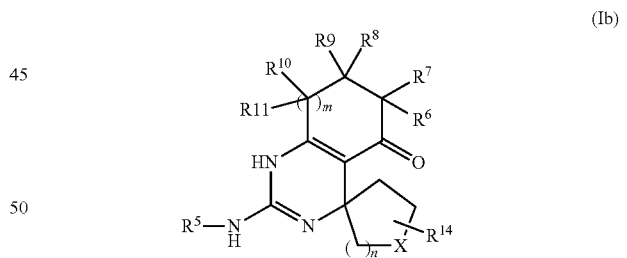

(Ib)

wherein X is selected from the group consisting of O, S, and SO$_2$, wherein R$^{14}$ is selected from the group consisting of hydrogen, alkyl, and aryl, and wherein n is 0, 1, or 2.

In accordance with an embodiment of the compound of formula (Ib), m is 1.

In an embodiment of these compounds, R$^6$, R$^7$, R$^8$, R$^9$, R$^{10}$, and R$^{11}$ are hydrogen.

In a preferred embodiment of these compounds, R$^8$ and R$^9$ are both hydrogen.

In another preferred embodiment of these compounds, R$^8$ and R$^9$ are both methyl.

In another preferred embodiment of these compounds, R$^8$ is hydrogen and R$^9$ is phenyl.

In keeping with the embodiments described above, specific examples of compounds include compounds selected from the group consisting of:
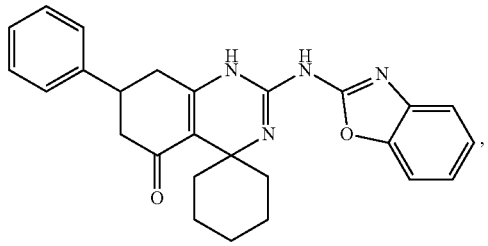
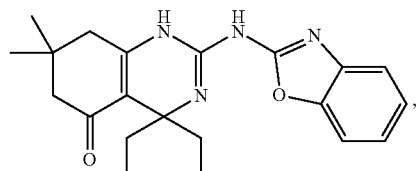
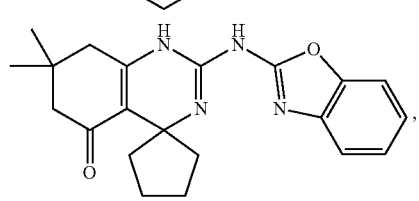
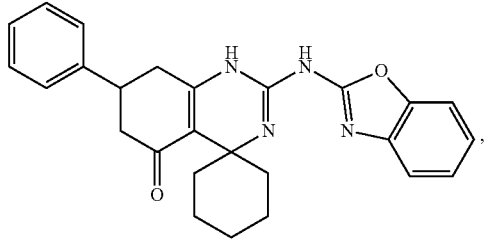
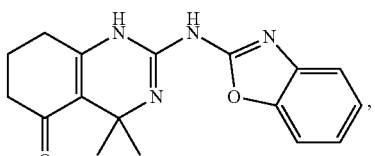
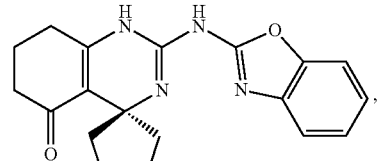
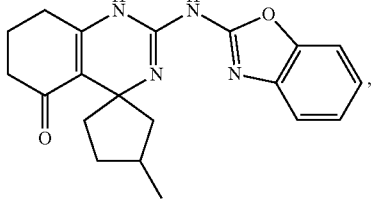
-continued
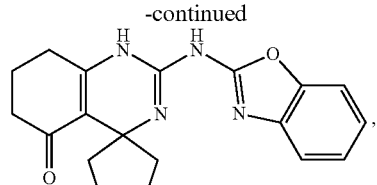
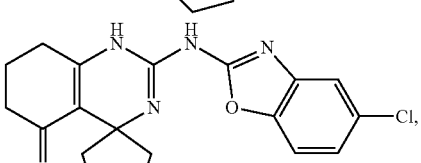
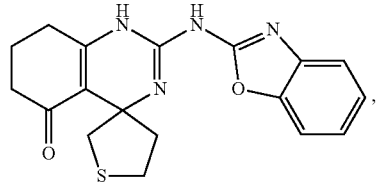
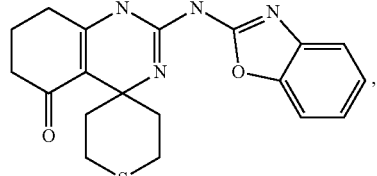
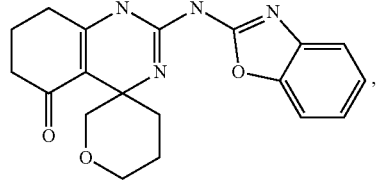
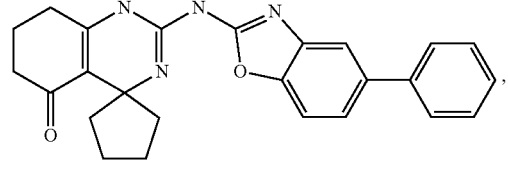
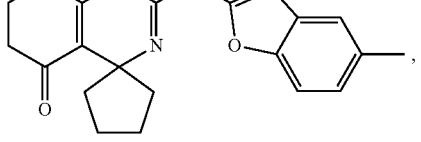
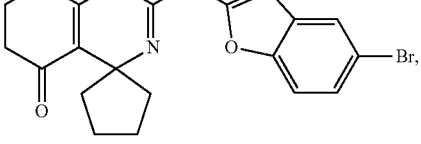
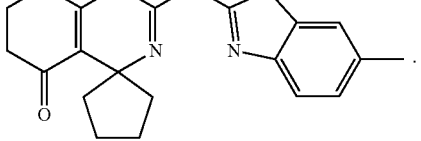

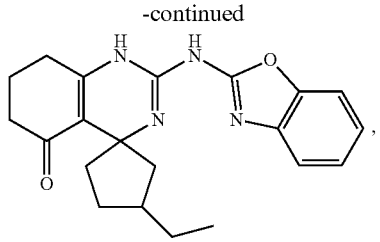

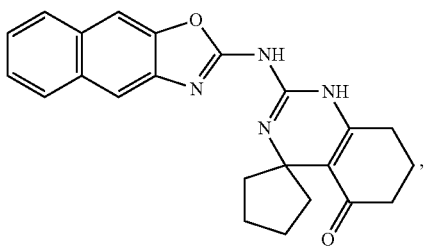

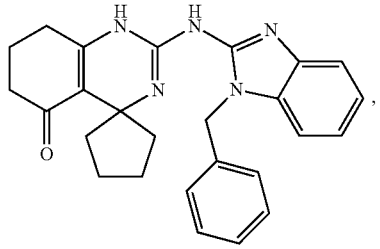

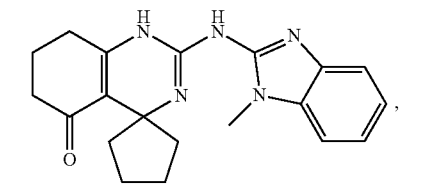

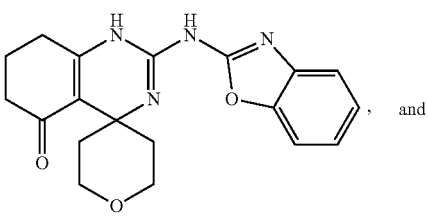

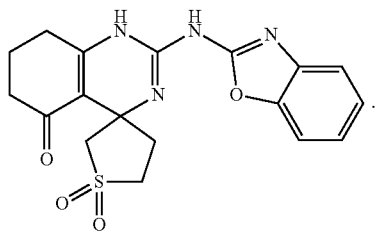

, and

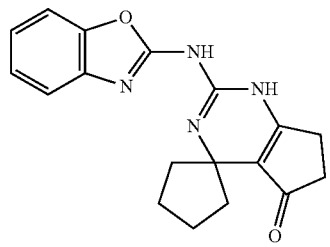

In accordance with an embodiment of the compounds of formula (I), R³ is selected from the group consisting of —NH-alkyl, —NH-cycloalkyl, —NH-aryl, —NH-alkylaryl, —NH-heteroaryl, —N-heteroaryl, and —NR$^{12}$R$^{13}$ wherein R$^{12}$ and R$^{13}$ are each independently selected from the group consisting of hydrogen, alkyl, cycloalkyl, aryl, arylalkyl, and heteroaryl, or wherein R$^{12}$ and R$^{13}$ together form a heteroaryl or a heterocycloalkyl, wherein R$^4$ is selected from the group consisting of hydrogen and alkyl, wherein R$^5$ is heteroaryl, and wherein alkyl, aryl, heterocycloalkyl, carbocyclic ring, heterocyclic ring, arylalkyl, and heteroaryl groups are unsubstituted or optionally substituted with one or more substituents selected from the group consisting of alkyl, aryl, halo, trifluoromethyl, alkoxy, aryloxy, amino, alkylamino, and dialkylamino.

In keeping with the embodiments described above, specific examples of compounds include compounds selected from the group consisting of:

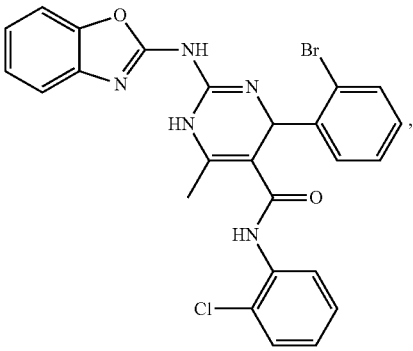

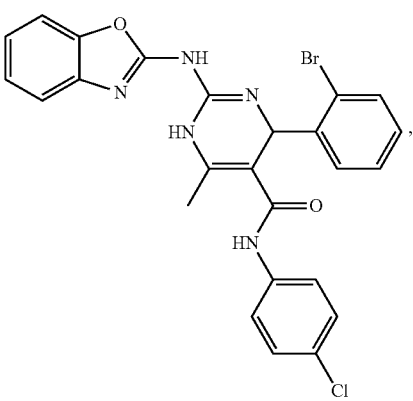

In accordance with an embodiment of the compound of formula (Ib), m is 0.

In an embodiment of these compounds, R$^6$, R$^7$, R$^8$, R$^9$, R$^{10}$, and R$^{11}$ are hydrogen.

In accordance with a specific embodiment of these compounds, the compound is

17
-continued
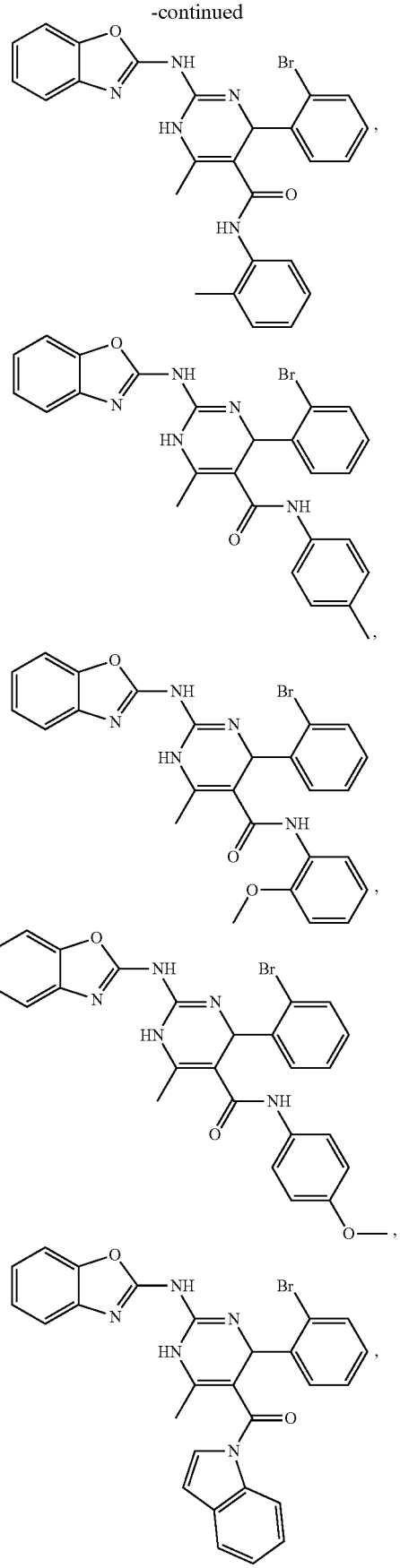
18
-continued
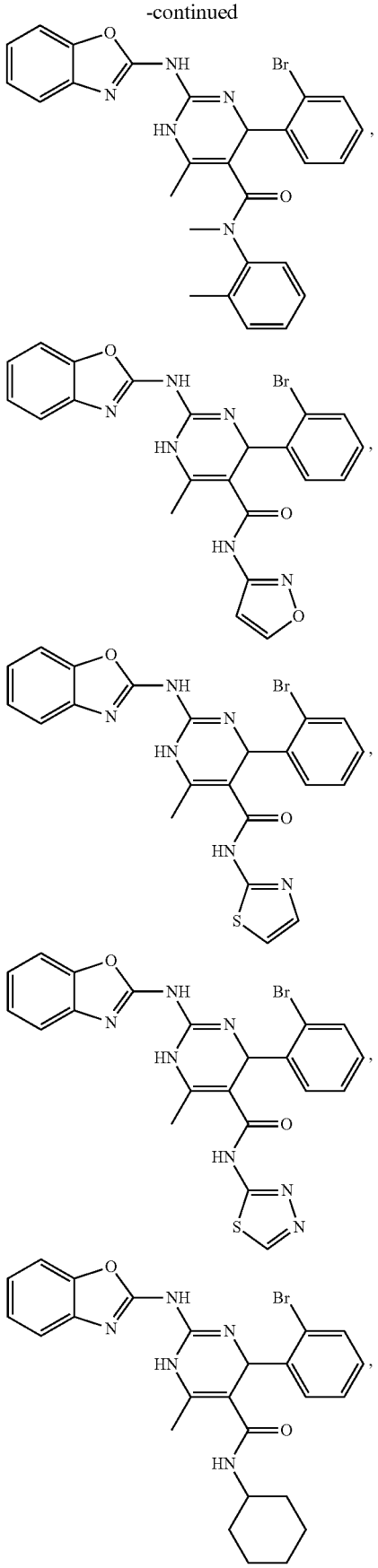

-continued
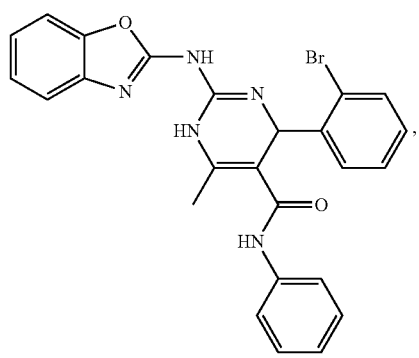
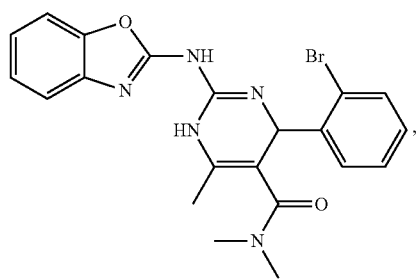
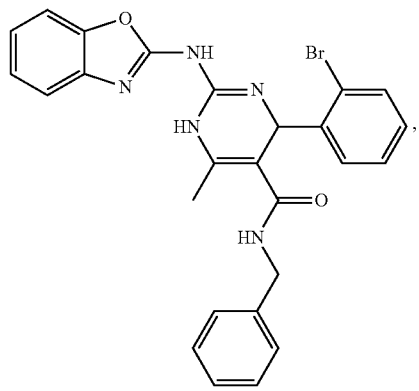
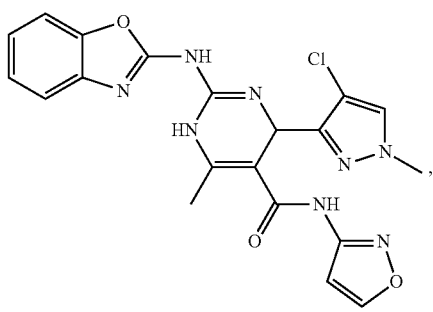
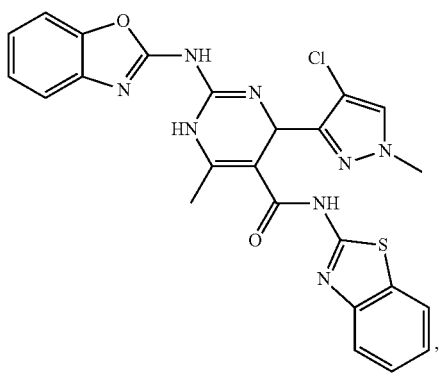
-continued
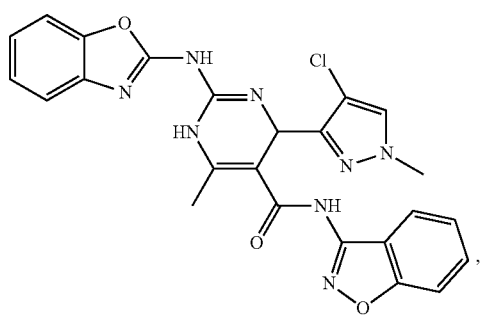
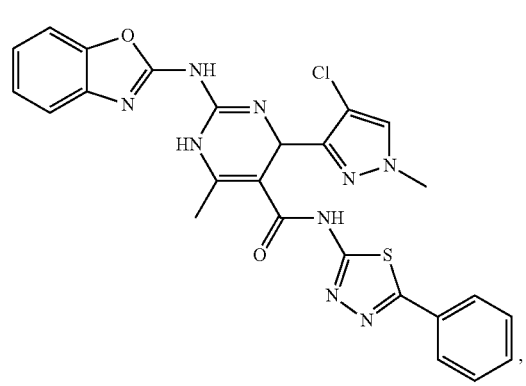
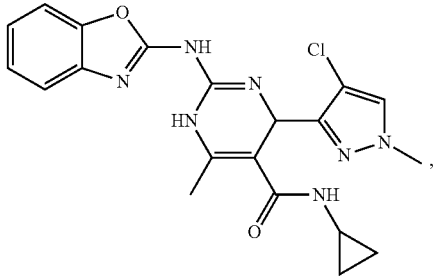
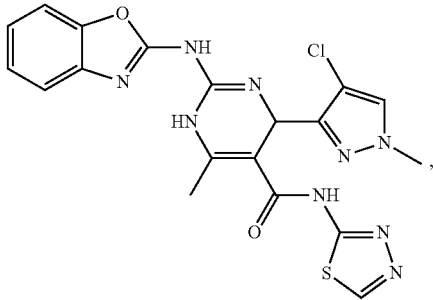
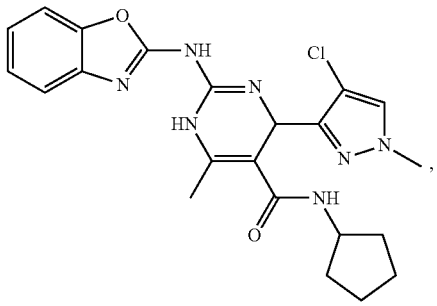

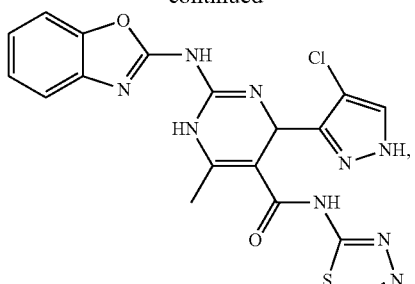

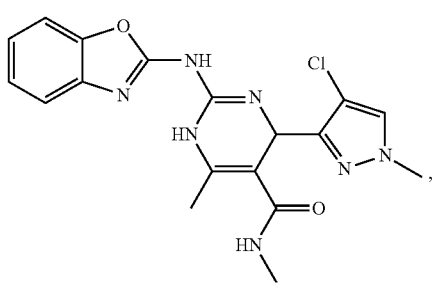

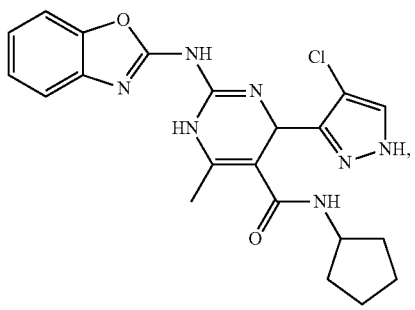

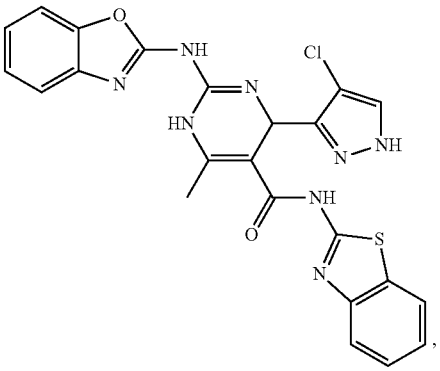

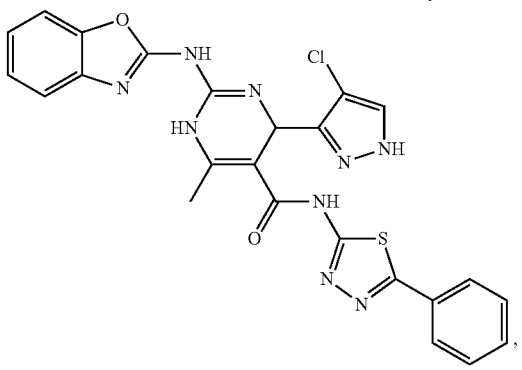

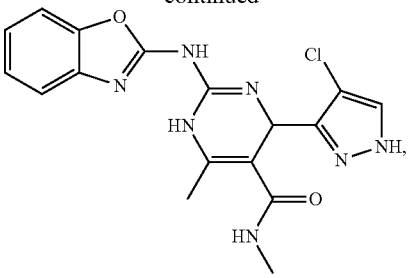

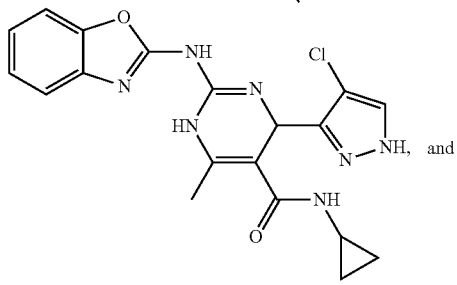

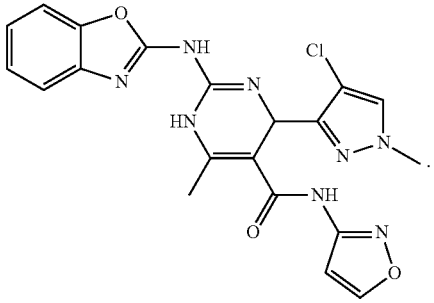

In accordance with an embodiment, the compound of formula (I) has the formula (Ic):

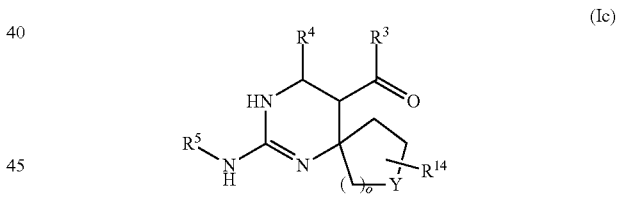

wherein $R^3$ is selected from the group consisting of —NH-alkyl, —NH-cycloalkyl, —NH-aryl, —NH-alkylaryl, —NH-heteroaryl, —N-heteroaryl, and —NR$^{12}$R$^{13}$ wherein $R^{12}$ and $R^{13}$ are each independently selected from the group consisting of hydrogen, alkyl, cycloalkyl, aryl, arylalkyl, and heteroaryl, or wherein $R^{12}$ and $R^{13}$ together form a heteroaryl or heterocycloalkyl, wherein $R^4$ is selected from the group consisting of hydrogen and alkyl, wherein Y is selected from the group consisting of CHR$^{10}$, O, S, and SO$_2$, wherein $R^{10}$ and $R^{14}$ are each independently selected from the group consisting of hydrogen, alkyl, and aryl optionally substituted with one or more substituents selected from the group consisting of halo, trifluoromethyl, alkyl, alkoxy, aryloxy, and dialkylamino, and wherein o is 0, 1, or 2.

In keeping with the embodiments described above, specific examples of compounds include compounds selected from the group consisting of:

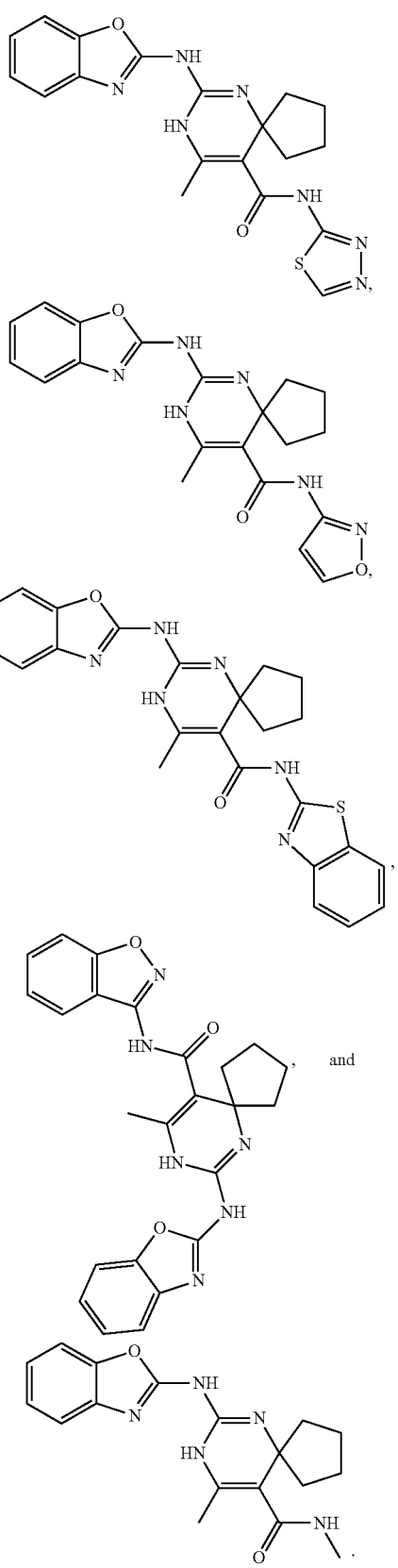

It will be understood that the position of double bonds in a dihydropyrimidinyl ring is not fixed and that any structure comprising a dihydropyrimidinyl ring also includes tautomers thereof. For example, the structure

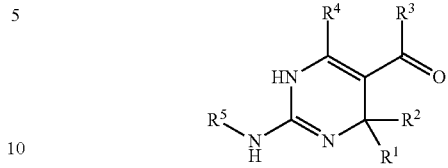

also is intended to refer to the tautomers

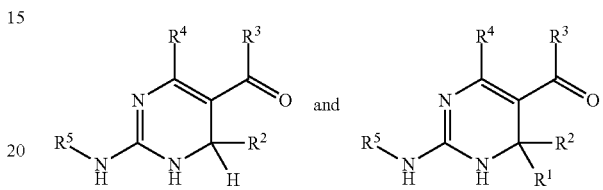

when $R^1$ and $R^2$ are not hydrogen;
and also when $R^1$ and/or $R^2$ are hydrogen to the tautomer

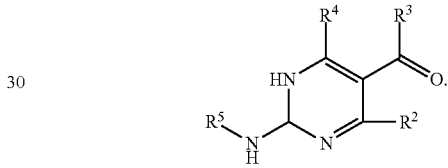

In any of the above embodiments, the compound or salt of formula (I) can have at least one asymmetric carbon atom. When the compound or salt has at least one asymmetric carbon atom, the compound or salt can exist in the racemic form, in the form of its pure optical isomers, or in the form of a mixture wherein one isomer is enriched relative to the other. In particular, in accordance with the present invention, when the inventive compounds have a single asymmetric carbon atom, the inventive compounds may exist as racemates, i.e., as mixtures of equal amounts of optical isomers, i.e., equal amounts of two enantiomers, or in the form of a single enantiomer. As used herein, "single enantiomer" is intended to include a compound that comprises more than 50% of a single enantiomer (i.e., enantiomeric excess up to 100% pure enantiomer).

When the compound or salt has more than one chiral center, the compound or salt can therefore exist as a mixture of diastereomers or in the form of a single diastereomer. As used herein, "single diastereomer" is intended to mean a compound that comprises more than 50% of a single diastereomer (i.e., diastereomeric excess to 100% pure diastereomer).

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceu-*

*tical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a quinoline group or a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

The present invention is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present invention chosen, as well as by the particular method used to administer the composition. Accordingly, there is a wide variety of suitable formulations of the pharmaceutical composition of the present invention. The following formulations for oral, aerosol, nasal, pulmonary, parenteral, subcutaneous, intravenous, intraarterial, intramuscular, intraperitoneal, intrathecal, intratumoral, topical, rectal, and vaginal administration are merely exemplary and are in no way limiting.

The pharmaceutical composition can be administered parenterally, e.g., intravenously, intraarterially, subcutaneously, intradermally, or intramuscularly. Thus, the invention provides compositions for parenteral administration that comprise a solution or suspension of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice,* J. B. Lippincott Company, Philadelphia, pp. 238-250 (1982), and Toissel, *ASHP Handbook on Injectable Drugs,* 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the present invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the aforedescribed pharmaceutical compositions, the compound or salt of the present invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

The invention further provides a method for treating or preventing a human galactokinase mediated disease or disorder in a mammal. The method comprises administering an effective amount of the compound of formula (I), salt thereof, enantiomers thereof, a mixture of enantiomers thereof, or diastereomers of the invention to a mammal afflicted therewith. Preferably, the mammal is a human.

The term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human. Furthermore, the subject can be the unborn offspring of any of the forgoing hosts, especially mammals (e.g., humans), in which case any screening of the subject or cells of the subject, or administration of compounds to the subject or cells of the subject, can be performed in utero.

The human galactokinase mediated disease or disorder is typically a disease or disorder wherein the production of galactose-1-phosphate is implicated in the development or progression of the disease or disorder. Patients having a deficiency in a galactose-1-phosphate uridyltransferase (GALT, EC 2.7.7.12) activity can have a potentially lethal disorder called classic galactosemia. GALT facilitates the conversion of uridine diphosphoglucose (UDP-glucose) and galactose-1-phosphate (gal-1-p) to uridine diphosphogalactose (UDP-galactose and glucose-1-phosphate. Consequently, GALT deficiency leads to the unique accumulation of gal-1-p and deficiency of UDP-galactose and UDP-glucose in patient cells. If untreated, classic galactosemia can result in severe disease in the newborn period, including liver dysfunction, quickly progressing to liver failure, coagulopathy, coma, and death.

In accordance with an embodiment, the invention provides a method of treating or preventing classic galactosemia comprising administering to a patient in need thereof a therapeutically effective amount of a compound represented by Formula (I) or a salt thereof.

In accordance with another embodiment, the invention provides a method of reducing the level of galactose-1-phosphate in a cell comprising contacting a cell with a therapeutically effective amount of a compound represented by Formula (I) or (II) or a salt thereof.

In accordance with another embodiment, the invention provides a method for treating or preventing a PTEN/AKT mis-regulated cancer in a mammal, comprising administering to the mammal in need of, a therapeutically or prophylactically effective amount of a compound represented by Formula (I) or a salt thereof. It has been reported that the galactose kinase 1 (GALK1) gene modifies the PTEN/AKT pathway in a number of human tissues and human cell lines, and that GALK1 mRNA is over-expressed in colon, head/neck, lung, ovary, pancreas, skin, and stomach tumors. GALK1 is well expressed in standard tumor cell lines including MDA-MB231T (breast tumor cell line), A549 (non-small cell lung tumor cell line,) U87MG (glioblastoma cell line) and PC-3 (prostate tumor cell line). Thus, inhibition of GALK1 may be useful in treatment of the aforesaid cancers.

"Treating" within the context of the present invention, means an alleviation of symptoms associated with a disorder or disease, or halt of further progression or worsening of those symptoms. For example, within the context of treating patients with classic galactosemia, successful treatment may be used in conjunction with dietary restrictions aimed at eliminating lactose and galactose in the diet. In addition, dietary restrictions are insufficient in treating galactosemia in some patients as the human body can produce galactose endogenously from the natural turnover of glycolipids and glycoproteins. Within the context of treating patients with classic galactosemia, successful treatment may include a reduction in clinical markers such as levels of galactose in blood or urine, and/or changes in clinical symptoms such as hepatomegaly (an enlarged liver), cirrhosis, renal failure, cataracts, brain damage, and ovarian failure, and the like. Treatment may also include administering the pharmaceutical formulations of the present invention in combination with other therapies. For example, the compounds and pharmaceutical formulations of the present invention may be administered on a chronic basis. The compounds of the invention can also be administered in conjunction with dietary restrictions.

"Preventing" within the context of the present invention, refers to a prophylactic treatment of an individual prone or subject to development of a condition, in particular, a disease or disorder responsive to inhibition of galactokinase. For example, those of skill in the medical arts may be able to determine, based on clinical symptoms and patient history, a statistical predisposition of a particular individual to the development of the aforesaid disease or disorder. For example, a family history of galactosemia can be used to assess the predisposition of a particular individual to the development of galactosemia and related disorders and thus inform the individual as to the desirability of preventative treatment with a compound or salt of the invention or a medicament formed therefrom. Accordingly, an individual predisposed to the development of a disease or disorder responsive to inhibition of galactokinase may be treated with a compound or a composition of the present invention in order to prevent, inhibit, reduce the effect of a development of, or slow the development of the disease or disorder or ameliorate the condition.

One skilled in the art will appreciate that suitable methods of utilizing a compound and administering it to a human for the treatment or prevention of disease states, in particular, classic galactosemia and cancers, e.g., colon, head/neck, lung, ovary, pancreas, skin, breast, non-small cell lung, glioblastoma, prostate, and stomach cancer, which would be useful in the method of the present invention, are available. Although more than one route can be used to administer a particular compound, a particular route can provide a more immediate and more effective reaction than another route. Accordingly, the described methods are merely exemplary and are in no way limiting.

The dose administered to a mammal, particularly, a human, in accordance with the present invention should be sufficient to effect the desired response. Such responses include reversal or prevention of the adverse effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the mammal.

By way of example and not intending to limit the invention, the dose of the pharmaceutically active agent(s) described herein for methods of preventing diseases or disorders, e.g., classic galactosemia and cancers, can be about 0.001 to about 1 mg/kg body weight of the subject being treated per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for methods of treating diseases or disorders, e.g., classic galactosemia and cancers, can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

The compounds of the invention can be synthesized by any suitable method, for example, by reacting a 1,3-dicarbonyl compound, an aldehyde, and a guanidine derivative to form the dihydropyrimidine ring. For example, the compounds of the invention can be synthesized according to the following route:

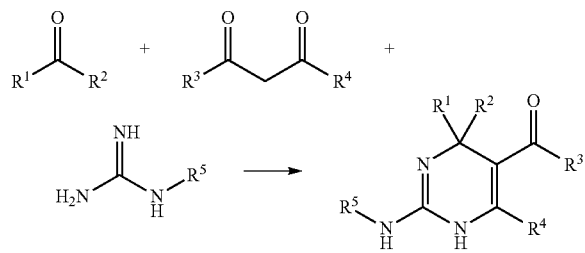

wherein $R^1$, $R^2$, $R^3$, $R^4$, and $R^5$ are as defined herein.

All air and/or moisture sensitive reactions were performed under positive pressure of nitrogen with oven-dried glassware. Anhydrous solvents such as dichloromethane, N,N-dimethylformamide (DMF), acetonitrile, methanol and triethylamine were obtained by purchasing from Sigma-Aldrich. Preparative purification was performed on a Waters semi-preparative HPLC. The column used was a Phenomenex Luna C18 (5 micron, 30×75 mm) at a flow rate of 45 ml/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nM). Analytical analysis was performed on an Agilent LC/MS (Agilent Technologies, Santa Clara, Calif.).

Method 1: A 7 minute gradient of 4% to 100% Acetonitrile (containing 0.025% trifluoroacetic acid) in water (containing 0.05% trifluoroacetic acid) was used with an 8 minute run time at a flow rate of 1 mL/min. A Phenomenex Luna C18 column (3 micron, 3×75 mm) was used at a temperature of 50° C.

Method 2: A 3 minute gradient of 4% to 100% Acetonitrile (containing 0.025% trifluoroacetic acid) in water (containing 0.05% trifluoroacetic acid) was used with a 4.5 minute run time at a flow rate of 1 mL/min. A Phenomenex Gemini Phenyl column (3 micron, 3×100 mm) was used at a temperature of 50° C.

Purity determination was performed using an Agilent Diode Array Detector on both Method 1 and Method 2. Mass determination was performed using an Agilent 6130 mass spectrometer with electrospray ionization in the positive mode. $^1$H NMR spectra were recorded on Varian 400 MHz spectrometers. Chemical Shifts are reported in ppm with tetramethylsilane (TMS) as internal standard (0 ppm) for $CDCl_3$ solutions or undeuterated solvent (DMSO-h6 at 2.49 ppm) for DMSO-d6 solutions. All of the analogs for assay have purity greater than 95% based on both analytical methods. High resolution mass spectrometry was recorded on an Agilent 6210 Time-of-Flight LC/MS system. Confirmation of molecular formula was accomplished using electrospray ionization in the positive mode with the Agilent Masshunter software (version B.02).

The following examples further illustrate the invention but, of course, should not be construed as in any way limiting its scope.

Example 1

This example demonstrates a synthesis of an exemplary compound in accordance with an embodiment of the invention.

Cyclohexane-1,3-dione (0.191 g, 1.703 mmol, 1.5 equiv.) and 1-(benzo[d]oxazol-2-yl)guanidine (0.2 g, 1.135 mmol, 1.0 equiv.) were added to a 2-5 ml Biotage microwave vial with a stir bar, and the powders were mixed well. Cyclopentanone (0.102 ml, 1.135 mmol, 1.5 equiv.) was added, then the microwave vial was capped and quickly dropped into an oil bath at 120° C. with vigorous stirring. The vial was stirred at 120° C. for 6 hours, then removed from the oil bath; the reaction flask was carefully vented using a needle, then the cap was removed and ~6 ml of DMSO was added to the hot flask. Once all of the compound has dissolved, purification was done by directly injecting to a Waters™ reverse phase purification system to give NCGC00187642/CID:664331 as a TFA salt (0.072 g, 14%).

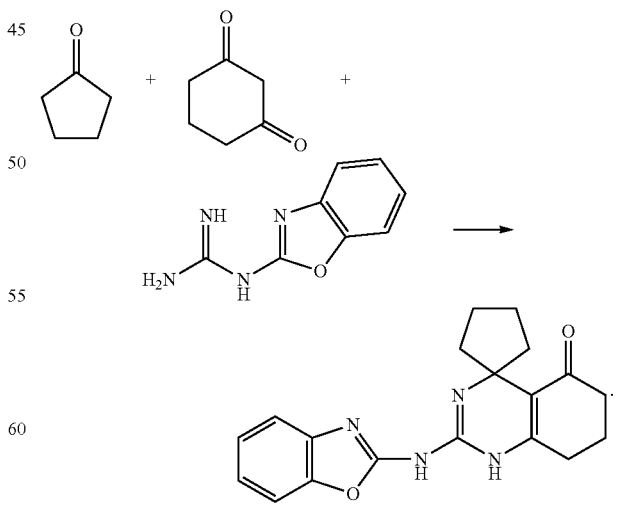

$^1$H NMR (400 MHz, DMSO-$d_6$); 10.37 (br. s. 1H), 9.98 (br. S. 1H), 7.40 (m, 2H), 7.16 (m, 2H), 2.52 (m, 2H), 2.39 (m, 2H), 2.26 (m, 2H), 1.83 (m, 6H), 1.62 (m, 2H). Method 1, retention time, 5.671 min; Method 2, retention time 3.704 min; HRMS: m/z (M+H+)=336.1592 (Calculated for $C_{19}H_{20}N_4O_2$=336.1586). Solubility (PBS, pH 7.4, 23° C.)=2.3 µg/ml.

Example 2

This example demonstrates a primary qHTS assay for inhibitors of GALK.

Assay details and protocol: The primary assay monitored ATP depletion using Promega's KinaseGlo™ technology, where ATP levels are measured through luminescence generated from firefly luciferase, a bioluminescent ATP-dependent enzymes. ATP was held at 35 µM, near its reported $K_M$ value, and the $K_M$ for galactose was determined under the 1536-well assay conditions to be 50-100M (FIG. 1A). As well, the $IC_{50}$ for a commercially available CD45 inhibitor (N-(9,10-dioxo-9,10-dihydrophenanthren-2-yl)pivalamide) was confirmed (previously found to inhibit GALK (FIG. 1B)). This was used as the positive control for the assay. The assay used 5 nM GALK and a 1 hr incubation time, which gave sufficient signal:background and stability for the HTS. The percent conversion of ATP under these conditions was estimated to be approximately 50% using an ATP standard curve.

Example 3

As in the primary screen, the confirmatory assay monitored ATP depletion using Promega's KinaseGlo™ technology, where ATP levels are measured through luminescence generated from firefly luciferase, a bioluminescent ATP-dependent enzymes, 6. ATP was held at 35 µM, near its reported $K_M$ value, and the $K_M$ for galactose was determined under the 1536-well assay conditions to be 50-100 µM.

Example 4

Secondary Assays

The selectivity for these analogs against CDP-ME kinase, another member of the GHMP kinase family, was performed using a bioluminescent Kinase Glo™ assay that detects ATP depletion after kinase reaction (PubChem ID 2506). NCGC00187642 (CID_664331); all analogs showed no activity in this assay (up to 57 µM), highlighting the selectivity of this chemotype. All analogs were also tested for cytotoxicity using Promega CellTiter Glo on HEK293 cells that were treated with compounds and analyzed after 48 hours. Compounds 3, 4, 6, 8, 10, 20, 26, 27, 28, 33, and 35 shown in table 1 showed no cytotoxic effect (PubChem ID 2547). In addition, the ability of these compounds to undergo redox recycling, which may lead to false positive results, was also evaluated using an endpoint colorimetric assay; this assay detects the presence of $H_2O_2$ in the kinase reaction buffer (PubChem ID 2502). The lead compound and analogs are inactive in the redox recycling, further confirming that these compounds have genuine GALK target activity.

Example 5

This example illustrates some of the properties of inventive compounds of formula I, in accordance with an embodiment of the invention.

The compounds set forth in Table 1 were screened against GALK using the primary qHTS assay described in Example 1. In addition, Table 1 presents the high resolution mass spectrometry molecular weight data for the inventive compounds.

TABLE 1

| | | GALK Assay | | High Resolution Mass Spec Data | | |
| --- | --- | --- | --- | --- | --- | --- |
| No. | Structure | IC50 (µM) | Efficacy | Exact MW | Calcd. [M + H] | Found [M + H] |
| 3 | | 16.7717 | 85.3762 | 322.142976 | 323.1503 | 323.1509 |
| 4 | | 4.2129 | 92.8022 | 336.158626 | 337.1659 | 337.1664 |
| 5 | | 32.6092 | 47.1996 | 310.142976 | 311.1503 | 311.1513 |

TABLE 1-continued

| No. | Structure | GALK Assay | | High Resolution Mass Spec Data | | |
| --- | --- | --- | --- | --- | --- | --- |
| | | IC50 (µM) | Efficacy | Exact MW | Calcd. [M + H] | Found [M + H] |
| 6 | 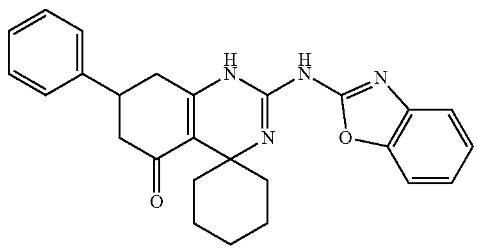 [SMILES: O=C1CC(c2ccccc2)CC2=C1C1(CCCCC1)N=C(Nc1nc3ccccc3o1)N2] | 42.1285 | 42.7443 | 426.205576 | 427.2129 | 427.2140 |
| 7 | 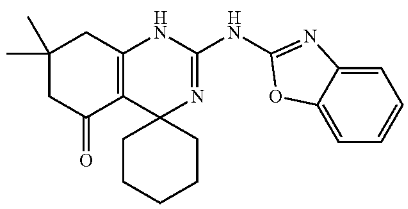 [SMILES: CC1(C)CC(=O)C2=C(C1)NC(Nc1nc3ccccc3o1)=NC21CCCCC1] | 5.1682 | 42.6121 | 378.205576 | 379.2129 | 379.2132 |
| 8 | 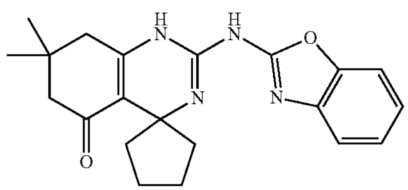 [SMILES: CC1(C)CC(=O)C2=C(C1)NC(Nc1nc3ccccc3o1)=NC21CCCC1] | 6.6769 | 86.616 | 364.189926 | 365.1972 | 365.1981 |
| 9 | 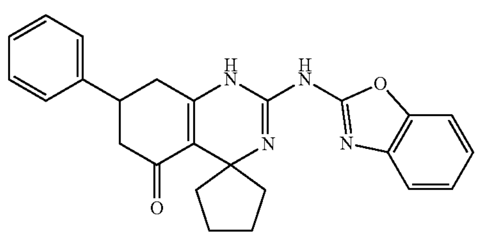 [SMILES: O=C1CC(c2ccccc2)CC2=C1C1(CCCC1)N=C(Nc1nc3ccccc3o1)N2] | 14.9478 | 40.4611 | 412.189926 | 413.1972 | 413.1988 |
| 10 | 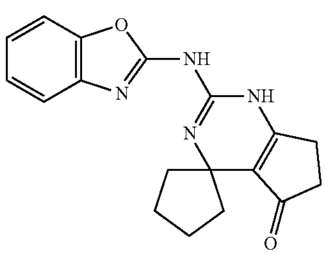 [SMILES: O=C1CCC2=C1C1(CCCC1)N=C(Nc1nc3ccccc3o1)N2] | 13.3222 | 79.8676 | 322.142976 | 323.1503 | 323.1515 |
| 12 | 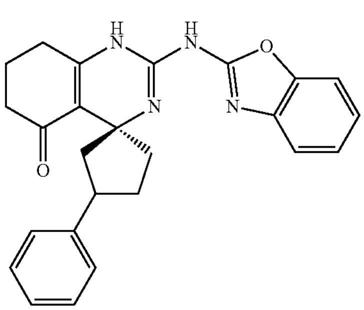 | 47.269 | 42.9838 | 412.189926 | 413.1972 | 413.1982 |

TABLE 1-continued

| | | GALK Assay | | High Resolution Mass Spec Data | | |
|---|---|---|---|---|---|---|
| No. | Structure | IC50 (μM) | Efficacy | Exact MW | Calcd. [M + H] | Found [M + H] |
| 14 | | 11.8734 | 79.2546 | 350.174276 | 351.1816 | 351.1823 |
| 16 | | 9.4314 | 60.4274 | 378.088353 | 379.0956 | 379.0968 |
| 17 | | 0.5951 | 79.2645 | 392.104004 | 393.1113 | 393.1118 |
| 19 | | 21.1143 | 40.3635 | 364.189926 | 365.1972 | 365.1987 |
| 20 | | 6.6769 | 71.2193 | 370.119654 | 371.1269 | 371.1279 |
| 21 | | 2.6581 | 88.8058 | 354.115047 | 355.1223 | 355.1235 |

TABLE 1-continued

| No. | Structure | GALK Assay IC50 (μM) | Efficacy | High Resolution Mass Spec Data Exact MW | Calcd. [M + H] | Found [M + H] |
|---|---|---|---|---|---|---|
| 22 | | 1.0582 | 77.7805 | 368.130697 | 369.1380 | 369.1392 |
| 23 | | 33.4639 | 56.2261 | 352.153541 | 353.1608 | 353.1615 |
| 24 | thiophene dioxide 2-(benzo[d]oxazol-2-ylamino)-4',5',7,8-tetrahydro-1H,2'H-spiro[quinazoline-4,3'-thiophen-1,1-dioxide]-5(6H)-one | 6.6769 | 67.583 | 386.104876 | 387.1122 | 387.1122 |
| 25 | | 18.8181 | 36.5021 | 412.189926 | 413.1972 | 413.1982 |
| 26 | | 5.9508 | 80.9702 | 350.174276 | 351.1816 | 351.1829 |
| 27 | | 7.4916 | 73.6075 | 414.069138 | 415.0764 | 415.0768 |
| 28 | | 21.1143 | 65.7113 | 350.174276 | 351.1816 | 351.1830 |

TABLE 1-continued

| | | GALK Assay | | High Resolution Mass Spec Data | | |
|---|---|---|---|---|---|---|
| No. | Structure | IC50 (μM) | Efficacy | Exact MW | Calcd. [M + H] | Found [M + H] |
| 29 | | 0 | 0 | 364.189926 | 365.1972 | 365.1979 |
| 33 | | 37.5471 | 32.1721 | 386.174276 | 387.1816 | 387.1824 |
| 34 | | 0 | 0 | 425.221561 | 426.2288 | |
| 35 | | 74.9163 | 32.4987 | 349.190260 | 350.1975 | 350.1984 |
| 36 | | 8.4057 | 70.3653 | 352.153541 | 353.1608 | 353.1616 |
| 37 | | 61.0781 | 36.3833 | 392.104004 | 393.1113 | 393.1112 |

TABLE 1-continued

| | | GALK Assay | | High Resolution Mass Spec Data | | |
|---|---|---|---|---|---|---|
| No. | Structure | IC50 (μM) | Efficacy | Exact MW | Calcd. [M + H] | Found [M + H] |
| 38 | | 68.5308 | 50.426 | 392.104004 | 393.1113 | 393.1118 |
| 39 | | 12.1867 | 95.0778 | 426.130360 | 427.1376 | 427.1389 |
| 40 | | 16.7717 | 21.752 | 426.130360 | 427.1376 | 427.1382 |
| 41 | | 0.7492 | 90.43 | 436.053488 | 437.0608 | 437.0628 |
| 42 | | 68.5308 | 42.0422 | 376.133554 | 377.1408 | 377.1411 |

TABLE 1-continued

|  |  | GALK Assay | | High Resolution Mass Spec Data | | |
|---|---|---|---|---|---|---|
| No. | Structure | IC50 (μM) | Efficacy | Exact MW | Calcd. [M + H] | Found [M + H] |
| 43 | | 48.5161 | 33.6539 | 388.153541 | 389.1608 | 389.1612 |
| 44 | | 18.8181 | 77.0421 | 388.153541 | 389.1608 | 389.1615 |
| 45 | | 61.0781 | 36.6772 | 388.153541 | 389.1608 | 389.1620 |
| 46 | | 61.0781 | 38.7514 | 372.158626 | 373.1659 | 373.1658 |
| 47 | | 61.0781 | 33.0611 | 372.158626 | 373.1659 | 373.1668 |

TABLE 1-continued

| No. | Structure | GALK Assay | | High Resolution Mass Spec Data | | |
|---|---|---|---|---|---|---|
| | | IC50 (μM) | Efficacy | Exact MW | Calcd. [M + H] | Found [M + H] |
| 48 | | 61.0781 | 69.6567 | 378.115047 | 379.1223 | 379.1222 |
| 49 | | 76.8928 | 43.3244 | 359.138225 | 360.1455 | 360.1464 |
| 50 | | 42.1285 | 25.6893 | 359.138225 | 360.1455 | 360.1465 |
| 51 | | 61.0781 | 51.6101 | 376.133554 | 377.1408 | 377.1415 |
| 52 | | 34.3468 | 96.8331 | 358.142976 | 359.1503 | 359.1513 |

TABLE 1-continued
| No. | Structure | GALK Assay IC50 (μM) | Efficacy | High Resolution Mass Spec Data Exact MW | Calcd. [M + H] | Found [M + H] |
|---|---|---|---|---|---|---|
| 53 | 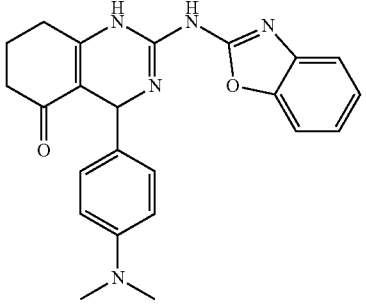 [SMILES: CN(C)c1ccc(C2N=C(Nc3nc4ccccc4o3)NC3=C2C(=O)CCC3)cc1] | 76.8928 | 42.2083 | 401.185175 | 402.1925 | 402.1926 |
| 55 | 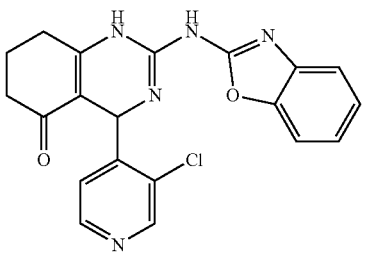 [SMILES: O=C1CCCC2=C1C(c1ccncc1Cl)N=C(Nc1nc3ccccc3o1)N2] | 15.3421 | 91.8683 | 393.099252 | 394.1065 | 394.1068 |
| 57 | 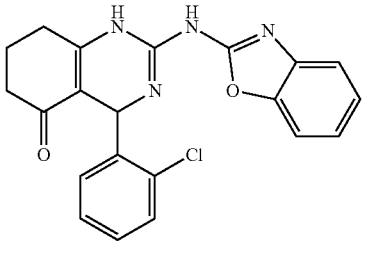 [SMILES: O=C1CCCC2=C1C(c1ccccc1Cl)N=C(Nc1nc3ccccc3o1)N2] | 2.6581 | 93.8521 | 392.104004 | 393.1113 | 393.1126 |
| 58 | 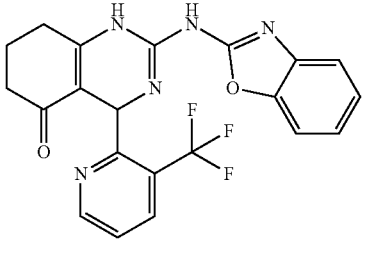 [SMILES: O=C1CCCC2=C1C(c1ncccc1C(F)(F)F)N=C(Nc1nc3ccccc3o1)N2] | 6.6769 | 91.8248 | 427.125609 | 428.1329 | 428.1338 |
| 59 | 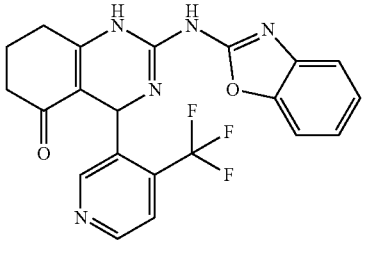 [SMILES: O=C1CCCC2=C1C(c1cnccc1C(F)(F)F)N=C(Nc1nc3ccccc3o1)N2] | 6.6769 | 95.2834 | 427.125609 | 428.1329 | 428.1327 |

TABLE 1-continued

| No. | Structure | GALK Assay | | High Resolution Mass Spec Data | | |
|---|---|---|---|---|---|---|
| | | IC50 (μM) | Efficacy | Exact MW | Calcd. [M + H] | Found [M + H] |
| 60 | 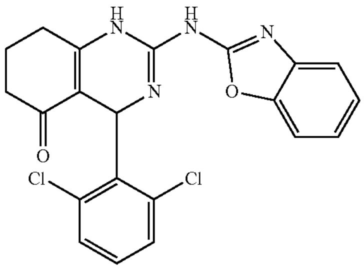 [SMILES: O=C1CCCC2=C1C(c1c(Cl)cccc1Cl)N=C(Nc1nc3ccccc3o1)N2] | 12.982 | 46.3283 | 426.065031 | 427.0723 | 427.0736 |
| 61 | 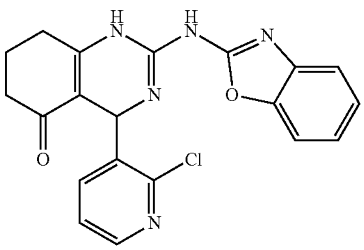 [SMILES: O=C1CCCC2=C1C(c1cccnc1Cl)N=C(Nc1nc3ccccc3o1)N2] | 18.8181 | 60.4156 | 393.099252 | 394.1065 | 394.1072 |
| 63 | 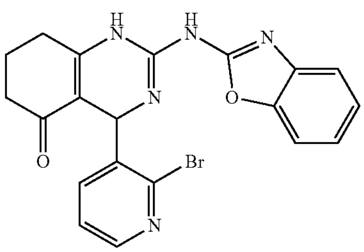 [SMILES: O=C1CCCC2=C1C(c1cccnc1Br)N=C(Nc1nc3ccccc3o1)N2] | 14.566 | 44.8906 | 437.048737 | 438.0560 | 438.0562 |
| 64 | 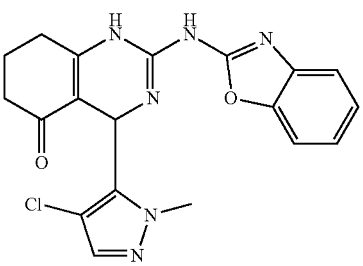 [SMILES: Cn1ncc(Cl)c1C1N=C(Nc2nc3ccccc3o2)NC2=C1C(=O)CCC2] | 36.5881 | 30.0153 | 396.110152 | 397.1174 | 397.1179 |
| 65 | 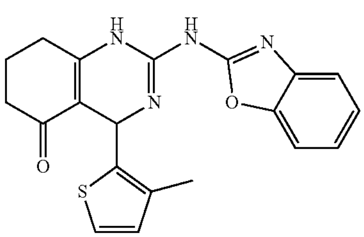 [SMILES: Cc1ccsc1C1N=C(Nc2nc3ccccc3o2)NC2=C1C(=O)CCC2] | 9.1905 | 98.61 | 378.115047 | 379.1223 | 379.1229 |
| 66 | 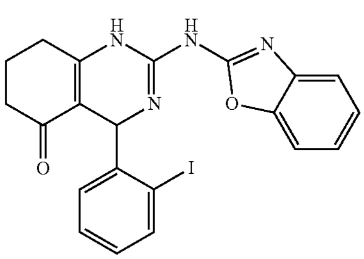 [SMILES: O=C1CCCC2=C1C(c1ccccc1I)N=C(Nc1nc3ccccc3o1)N2] | 1.157 | 86.1547 | 484.039619 | 485.0469 | 485.0480 |

TABLE 1-continued

| No. | Structure | GALK Assay | | High Resolution Mass Spec Data | | |
|---|---|---|---|---|---|---|
| | | IC50 (μM) | Efficacy | Exact MW | Calcd. [M + H] | Found [M + H] |
| 67 | 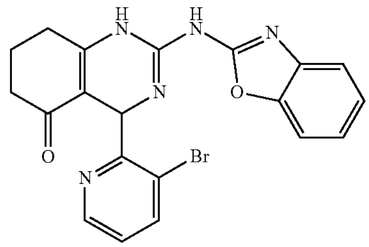 [SMILES: O=C1CCCC2=C1C(c1ncccc1Br)N=C(Nc1nc3ccccc3o1)N2] | 0.6506 | 73.7449 | 437.048737 | 438.0560 | 438.0570 |
| 68 | 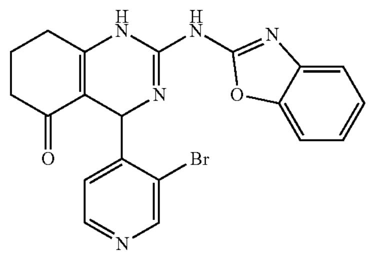 [SMILES: O=C1CCCC2=C1C(c1ccncc1Br)N=C(Nc1nc3ccccc3o1)N2] | 1.4566 | 90.2363 | 437.048737 | 438.0560 | 438.0570 |
| 69 | 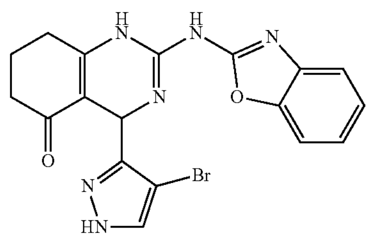 [SMILES: O=C1CCCC2=C1C(c1n[nH]cc1Br)N=C(Nc1nc3ccccc3o1)N2] | 2.9063 | 97.082 | 426.043986 | 427.0513 | 427.0519 |
| 70 | 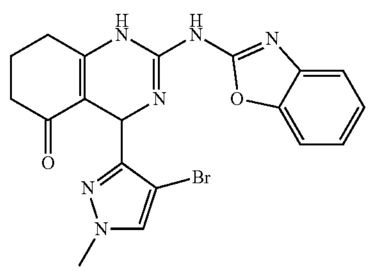 [SMILES: Cn1cc(Br)c(C2N=C(Nc3nc4ccccc4o3)NC3=C2C(=O)CCC3)n1] | 2.9063 | 94.0642 | 440.059636 | 441.0669 | 441.0675 |
| 71 | 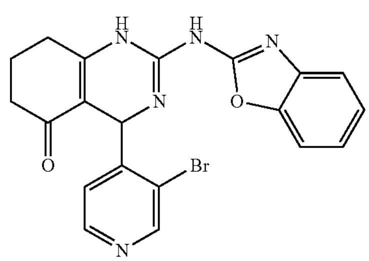 [SMILES: O=C1CCCC2=C1C(c1ccncc1Br)N=C(Nc1nc3ccccc3o1)N2] | 20.575 | 59.2065 | 437.048737 | 438.0560 | 438.0575 |
| 73 | 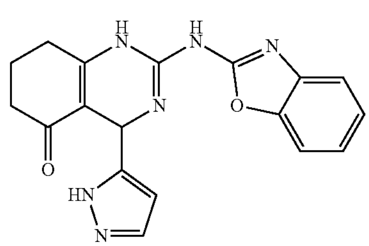 [SMILES: O=C1CCCC2=C1C(c1ccn[nH]1)N=C(Nc1nc3ccccc3o1)N2] | 14.566 | 56.9903 | 348.133474 | 349.1408 | 349.1410 |

TABLE 1-continued

| | | GALK Assay | | High Resolution Mass Spec Data | | |
|---|---|---|---|---|---|---|
| No. | Structure | IC50 (μM) | Efficacy | Exact MW | Calcd. [M + H] | Found [M + H] |
| 74 | | 18.3375 | 64.1609 | 362.149124 | 363.1564 | 363.1576 |
| 75 | | 2.9063 | 69.6318 | 382.094501 | 383.1018 | 405.0853 [M + 23] |
| 76 | | 3.2609 | 69.0891 | 535.041065 | 536.0483 | 536.0471 |
| 77 | | 5.1682 | 54.5237 | 535.041065 | 536.0483 | 536.0482 |

TABLE 1-continued

| | | GALK Assay | | High Resolution Mass Spec Data | | |
|---|---|---|---|---|---|---|
| No. | Structure | IC50 (μM) | Efficacy | Exact MW | Calcd. [M + H] | Found [M + H] |
| 78 | | 4.6062 | 72.3078 | 515.095688 | 516.1030 | 516.1052 |
| 79 | | 4.1053 | 67.2792 | 515.095688 | 516.1030 | 516.1051 |
| 80 | | 3.6588 | 56.7556 | 531.090602 | 532.0979 | 532.0981 |
| 81 | | 3.2609 | 83.3298 | 531.090602 | 532.0979 | 532.0989 |

TABLE 1-continued

| No. | Structure | GALK Assay | | High Resolution Mass Spec Data | | |
|---|---|---|---|---|---|---|
| | | IC50 (μM) | Efficacy | Exact MW | Calcd. [M + H] | Found [M + H] |
| 82 | 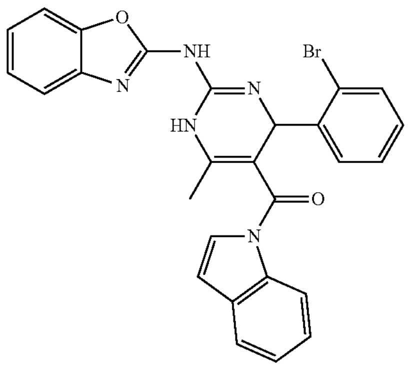 [SMILES: CC1=C(C(=O)n2ccc3ccccc32)C(c2ccccc2Br)N=C(Nc2nc3ccccc3o2)N1] | 18.3375 | 36.4861 | 525.080038 | 526.0873 | 526.0863 |
| 83 | 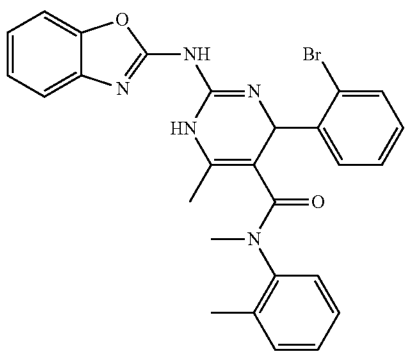 [SMILES: CC1=C(C(=O)N(C)c2ccccc2C)C(c2ccccc2Br)N=C(Nc2nc3ccccc3o2)N1] | 10.3119 | 39.4724 | 529.111338 | 530.1186 | 530.1200 |
| 84 | 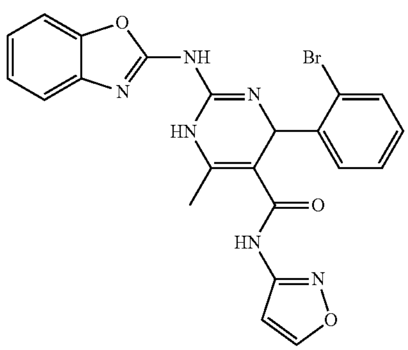 [SMILES: CC1=C(C(=O)Nc2ccon2)C(c2ccccc2Br)N=C(Nc2nc3ccccc3o2)N1] | 5.7988 | 85.8512 | 492.054551 | 493.0618 | 493.0639 |
| 85 | 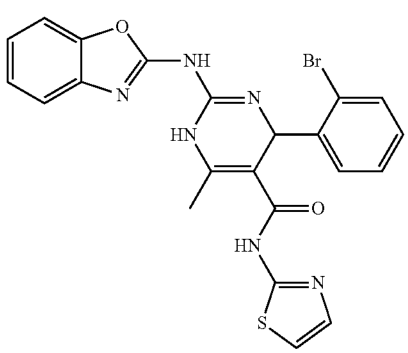 [SMILES: CC1=C(C(=O)Nc2nccs2)C(c2ccccc2Br)N=C(Nc2nc3ccccc3o2)N1] | 4.1053 | 43.3555 | 508.031707 | 509.0390 | 509.0407 |

TABLE 1-continued

| | | GALK Assay | | High Resolution Mass Spec Data | | |
|---|---|---|---|---|---|---|
| No. | Structure | IC50 (μM) | Efficacy | Exact MW | Calcd. [M + H] | Found [M + H] |
| 86 | | 3.2609 | 89.641 | 509.026956 | 510.0342 | 510.0355 |
| 87 | | 0 | 0 | 426.043986 | 427.0513 | 427.0514 |
| 89 | | 9.1905 | 61.8961 | 507.126988 | 508.1343 | 508.1358 |
| 90 | | 9.1905 | 64.6859 | 501.080038 | 502.0873 | 502.0889 |

TABLE 1-continued

| | | GALK Assay | | High Resolution Mass Spec Data | | |
|---|---|---|---|---|---|---|
| No. | Structure | IC50 (μM) | Efficacy | Exact MW | Calcd. [M + H] | Found [M + H] |
| 91 | | 20.575 | 61.1653 | 453.080038 | 454.0873 | 454.0878 |
| 92 | | 6.5064 | 66.4427 | 515.095688 | 516.1030 | 516.1040 |
| 93 | | 3.2609 | 91.774 | 409.132094 | 410.1394 | 410.1392 |
| 94 | | 6.5064 | 89.4844 | 392.159689 | 393.1670 | 393.1683 |

TABLE 1-continued
| No. | Structure | GALK Assay | | High Resolution Mass Spec Data | | |
|---|---|---|---|---|---|---|
| | | IC50 (μM) | Efficacy | Exact MW | Calcd. [M + H] | Found [M + H] |
| 95 | 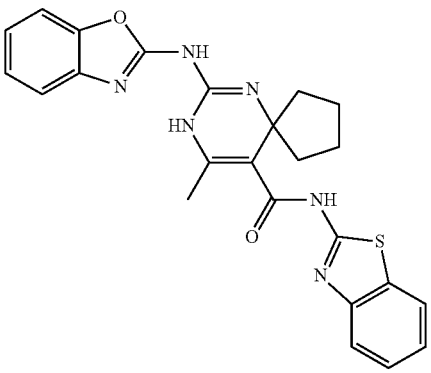 [SMILES: CC1=C(C(=O)Nc2nc3ccccc3s2)C2(CCCC2)N=C(Nc2nc3ccccc3o2)N1] | 25.9024 | 30.4548 | 458.152495 | 459.1598 | 459.1610 |
| 96 | 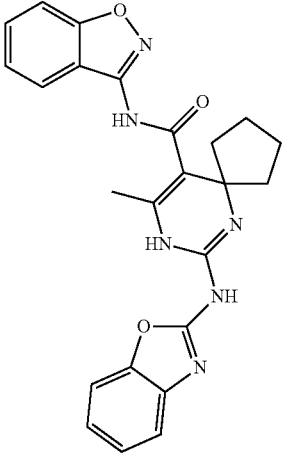 [SMILES: CC1=C(C(=O)Nc2noc3ccccc23)C2(CCCC2)N=C(Nc2nc3ccccc3o2)N1] | 0 | 0 | 442.175339 | 443.1826 | 443.1830 |
| 97 | 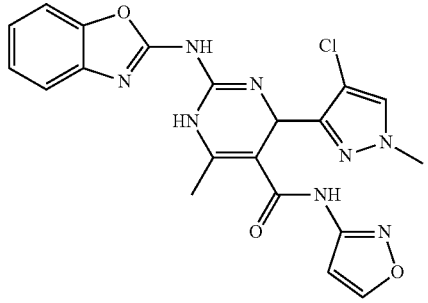 [SMILES: CC1=C(C(=O)Nc2ccon2)C(c2nn(C)cc2Cl)N=C(Nc2nc3ccccc3o2)N1] | 8.1911 | 77.2742 | 452.111214 | 453.1185 | 453.1195 |
| 98 | 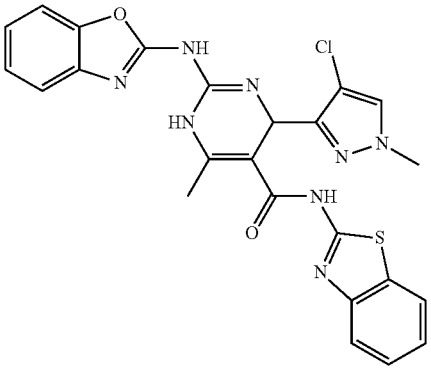 [SMILES: CC1=C(C(=O)Nc2nc3ccccc3s2)C(c2nn(C)cc2Cl)N=C(Nc2nc3ccccc3o2)N1] | 9.1905 | 25.4219 | 518.104020 | 519.1113 | 519.1128 |

TABLE 1-continued
| | | GALK Assay | | High Resolution Mass Spec Data | | |
| | | IC50 | | | Calcd. | Found |
| No. | Structure | (μM) | Efficacy | Exact MW | [M + H] | [M + H] |
| 99 | 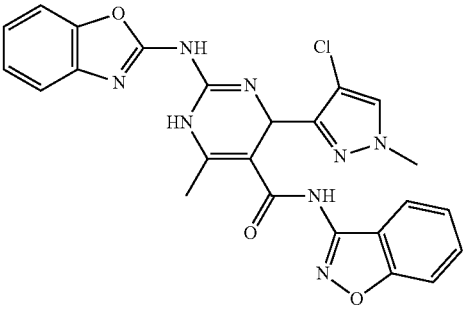 [SMILES: CC1=C(C(=O)Nc2noc3ccccc23)C(c2nn(C)cc2Cl)N=C(Nc2nc3ccccc3o2)N1] | 0 | 0 | 502.126864 | 503.1341 | 503.1351 |
| 100 | 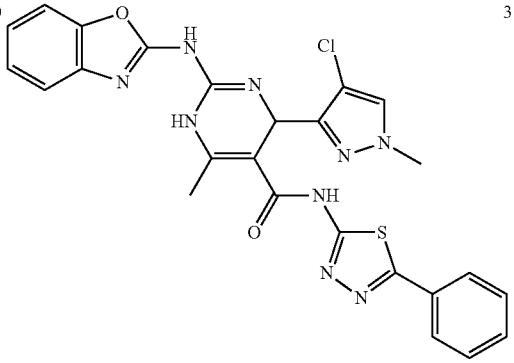 [SMILES: CC1=C(C(=O)Nc2nnc(-c3ccccc3)s2)C(c2nn(C)cc2Cl)N=C(Nc2nc3ccccc3o2)N1] | 3.6588 | 50.3529 | 545.114919 | 546.1222 | 546.1236 |
| 101 | 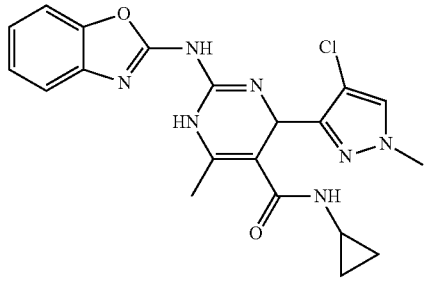 [SMILES: CC1=C(C(=O)NC2CC2)C(c2nn(C)cc2Cl)N=C(Nc2nc3ccccc3o2)N1] | 18.3375 | 59.169 | 425.136701 | 426.1440 | 426.1455 |
| 102 | 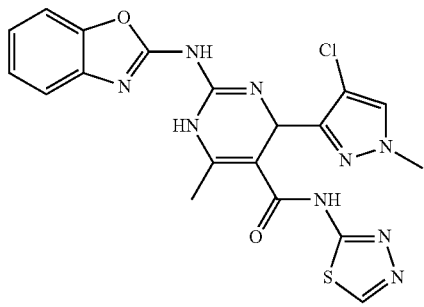 [SMILES: CC1=C(C(=O)Nc2nncs2)C(c2nn(C)cc2Cl)N=C(Nc2nc3ccccc3o2)N1] | 5.1682 | 75.2589 | 469.083619 | 470.0909 | 470.0914 |

TABLE 1-continued
| No. | Structure | GALK Assay | | High Resolution Mass Spec Data | | |
|---|---|---|---|---|---|---|
| | | IC50 (μM) | Efficacy | Exact MW | Calcd. [M + H] | Found [M + H] |
| 105 | 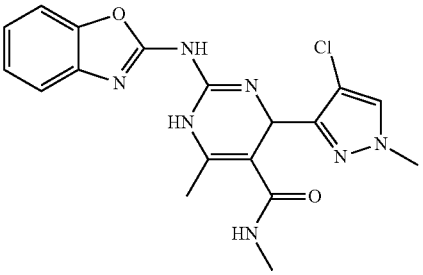 [SMILES: CNC(=O)C1=C(C)NC(Nc2nc3ccccc3o2)=NC1c1nn(C)cc1Cl] | 16.3433 | 64.736 | 399.121051 | 400.1283 | 400.1294 |
| 106 | 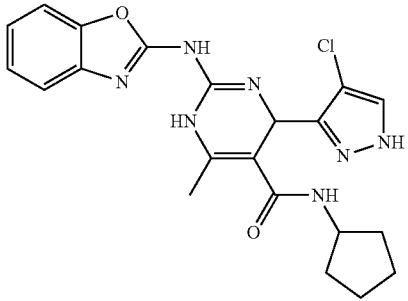 [SMILES: CC1=C(C(=O)NC2CCCC2)C(c2n[nH]cc2Cl)N=C(Nc2nc3ccccc3o2)N1] | 16.3433 | 69.0182 | 453.168001 | 454.1753 | 454.1762 |
| 107 | 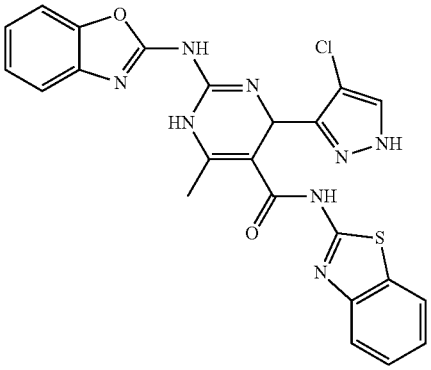 [SMILES: CC1=C(C(=O)Nc2nc3ccccc3s2)C(c2n[nH]cc2Cl)N=C(Nc2nc3ccccc3o2)N1] | 11.5702 | 28.7995 | 504.088370 | 505.0957 | 505.0973 |
| 108 | 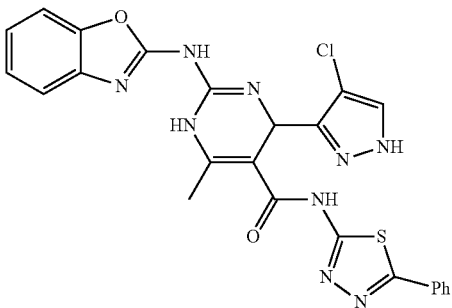 [SMILES: CC1=C(C(=O)Nc2nnc(-c3ccccc3)s2)C(c2n[nH]cc2Cl)N=C(Nc2nc3ccccc3o2)N1] | 5.1682 | 66.4502 | 531.099269 | 532.1065 | 532.1070 |

TABLE 1-continued

| No. | Structure | GALK Assay | | High Resolution Mass Spec Data | | |
|---|---|---|---|---|---|---|
| | | IC50 (μM) | Efficacy | Exact MW | Calcd. [M + H] | Found [M + H] |
| 109 | 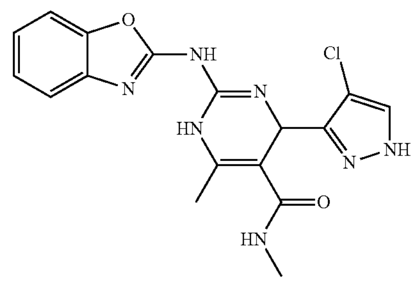 [SMILES: CNC(=O)C1=C(C)NC(Nc2nc3ccccc3o2)=NC1c1n[nH]cc1Cl] | 18.3375 | 54.0161 | 385.105401 | 386.1127 | 386.1139 |
| 110 | 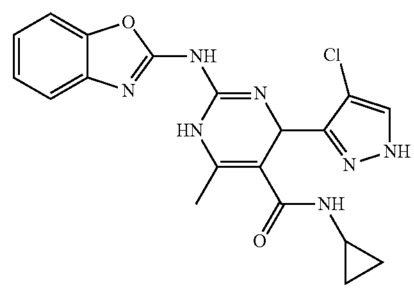 [SMILES: CC1=C(C(=O)NC2CC2)C(c2n[nH]cc2Cl)N=C(Nc2nc3ccccc3o2)N1] | 20.575 | 47.4384 | 411.121051 | 412.1283 | 412.1294 |
| 111 | 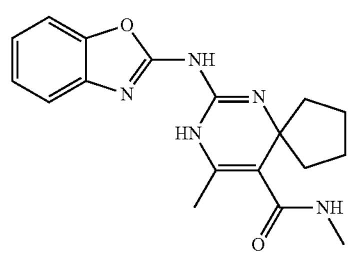 [SMILES: CNC(=O)C1=C(C)NC(Nc2nc3ccccc3o2)=NC12CCCC2] | 20.575 | 24.5579 | 339.169525 | 340.1768 | 340.1776 |
| 112 | 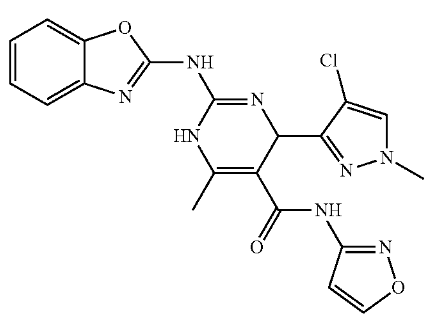 [SMILES: CC1=C(C(=O)Nc2ccon2)C(c2nn(C)cc2Cl)N=C(Nc2nc3ccccc3o2)N1] | 9.1905 | 86.5744 | 452.111214 | 453.1185 | 453.1195 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound selected from the group consisting of:

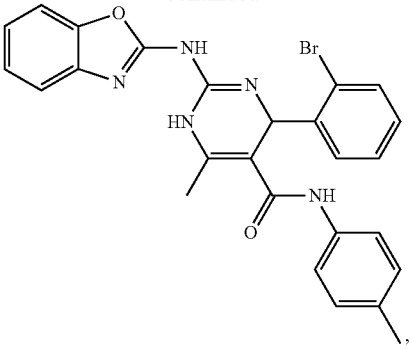

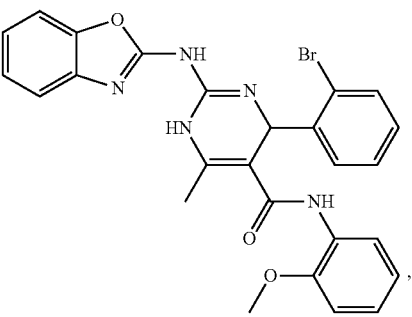

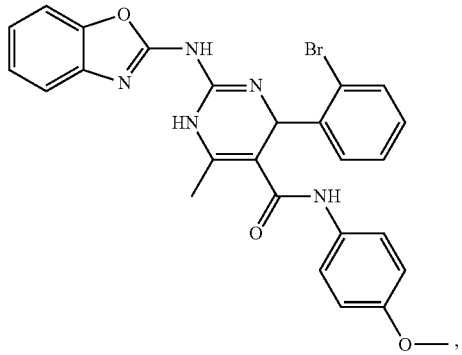

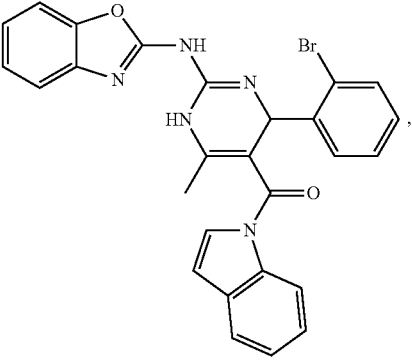

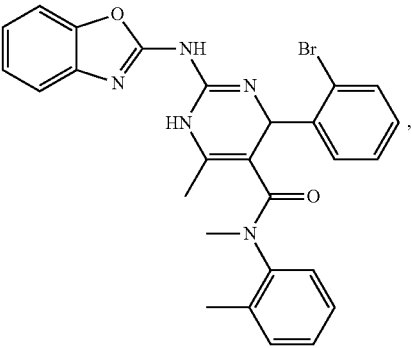

75
-continued
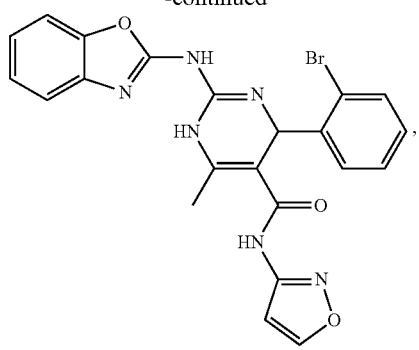
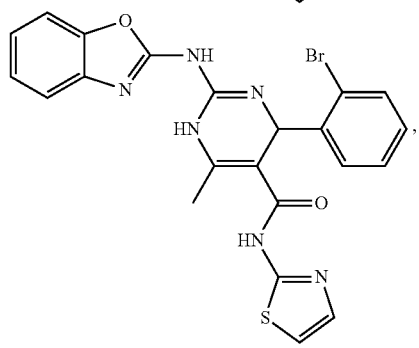
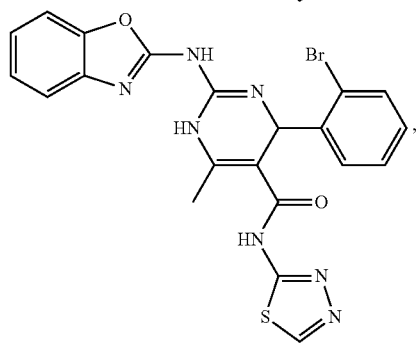
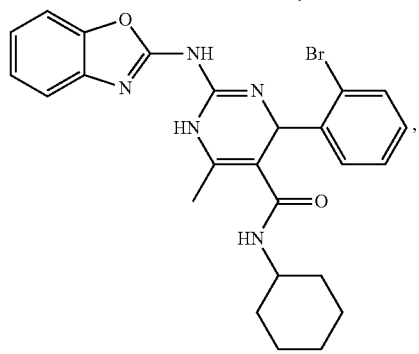
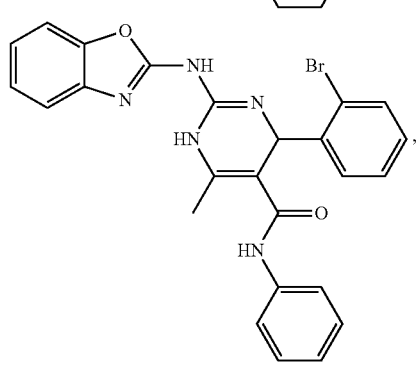
76
-continued
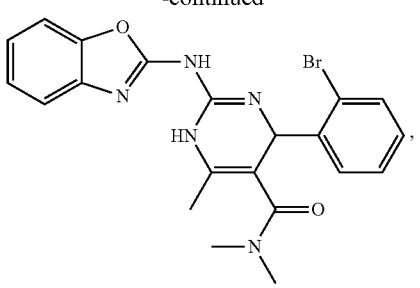
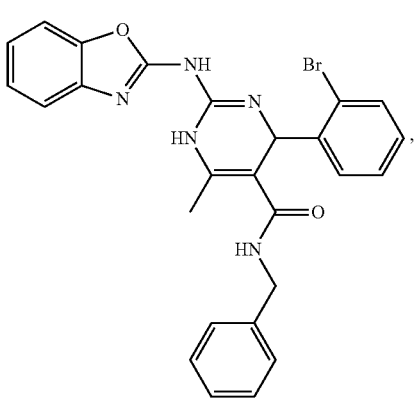
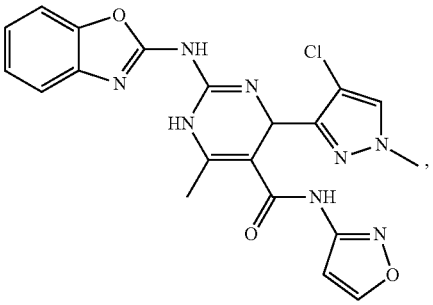
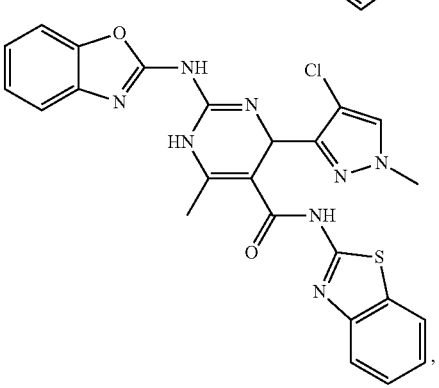
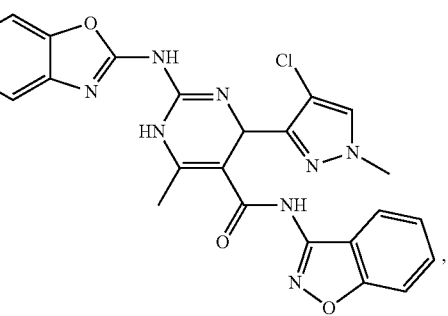

77
-continued
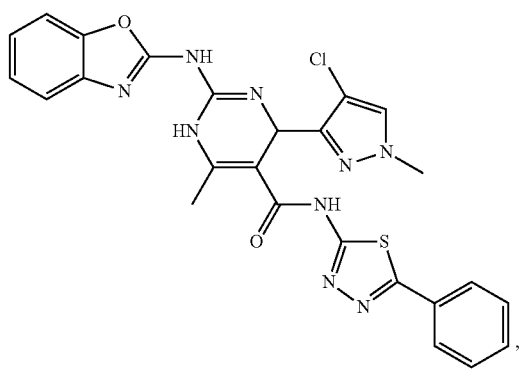
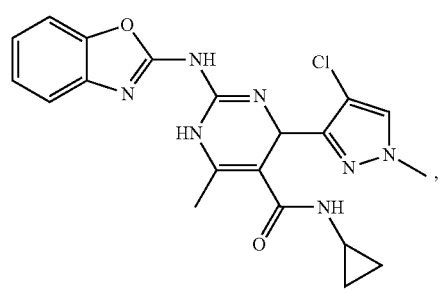
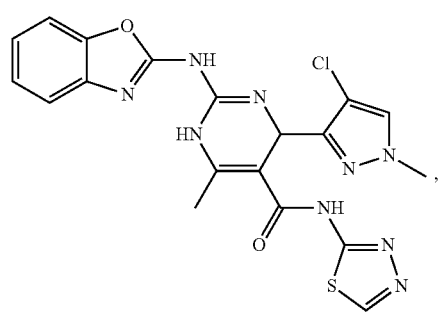
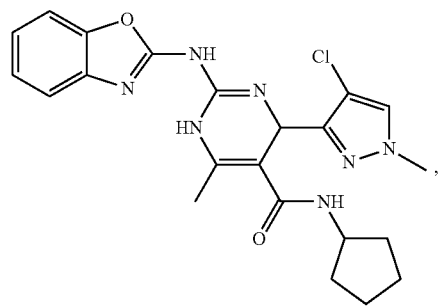
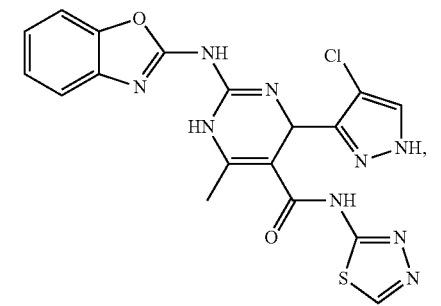
78
-continued
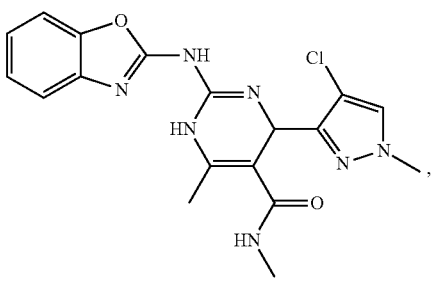
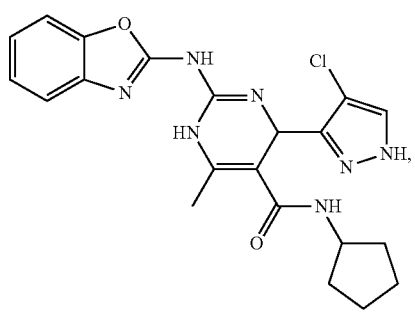
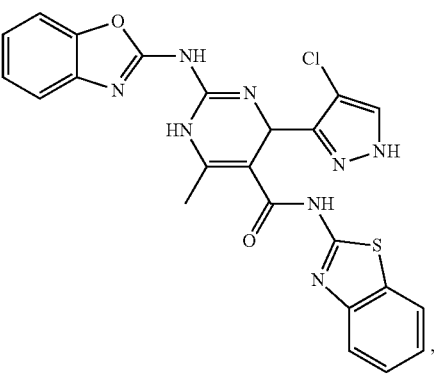
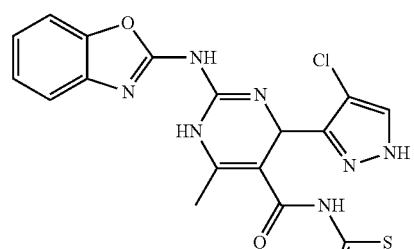
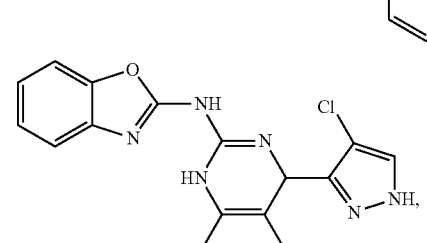

-continued
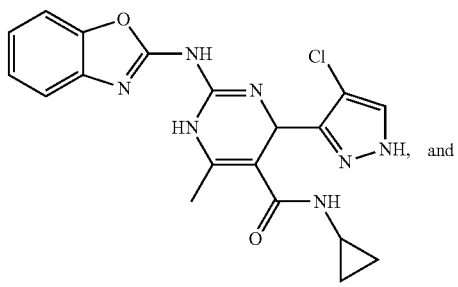
and
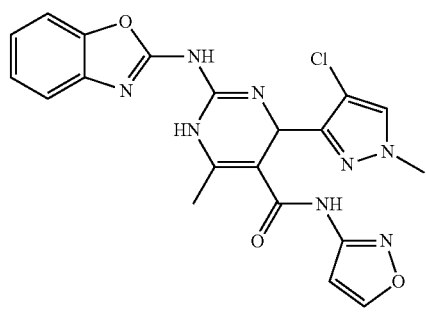
or a pharmaceutically acceptable salt thereof.
2. The compound or salt of claim 1, wherein the compound is selected from the group consisting of:
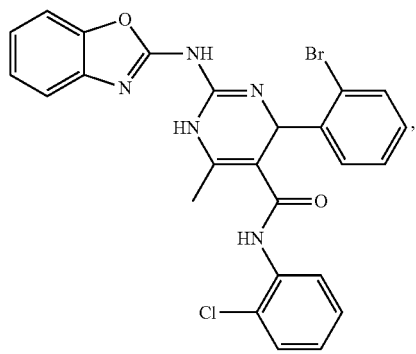
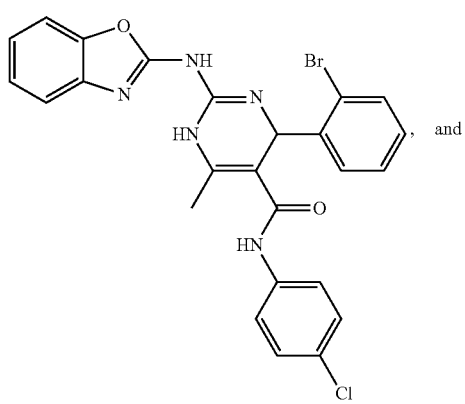
, and
-continued
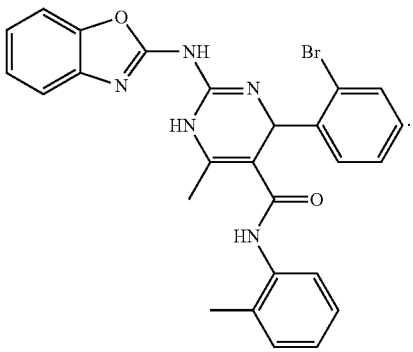
3. The compound or salt of claim 1, wherein the compound is selected from the group consisting of:
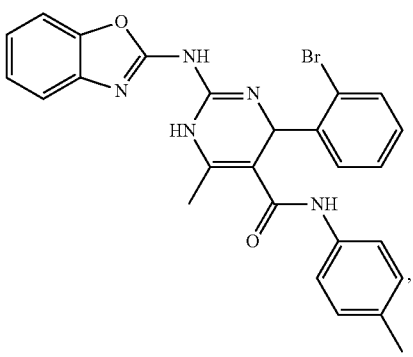
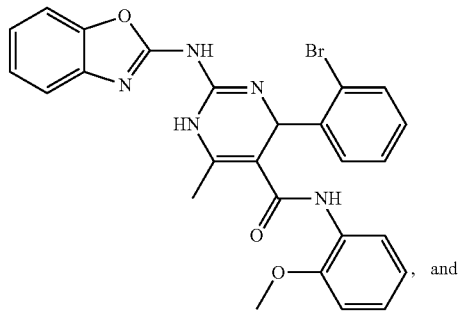
, and
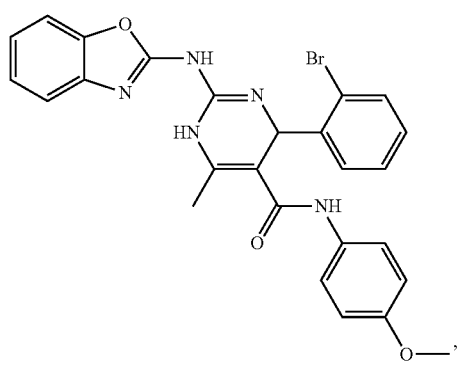
4. The compound or salt of claim 1, wherein the compound is selected from the group consisting of:

81
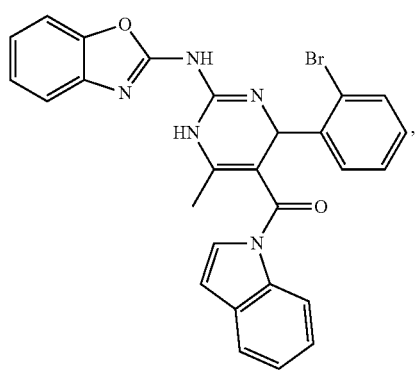
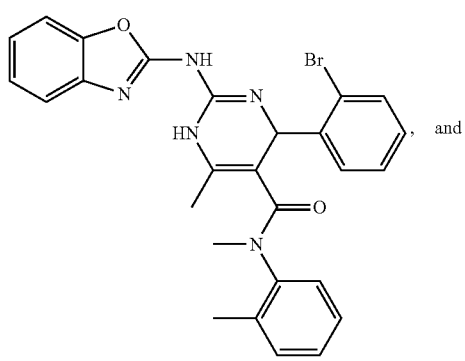
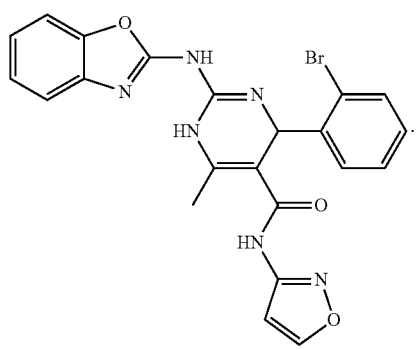
5. The compound or salt of claim 1, wherein the compound is selected from the group consisting of:
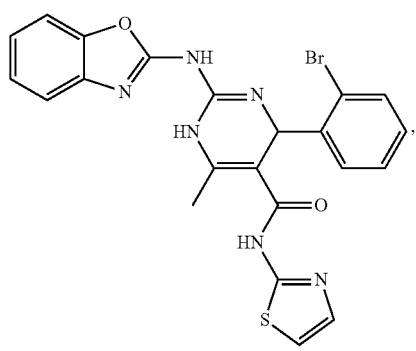
82
-continued
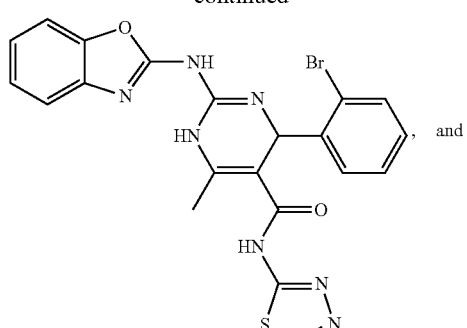
and
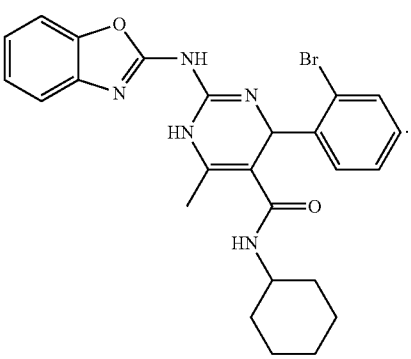
6. The compound or salt of claim 1, wherein the compound is selected from the group consisting of:
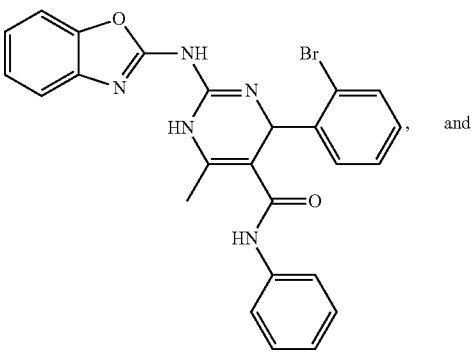
and
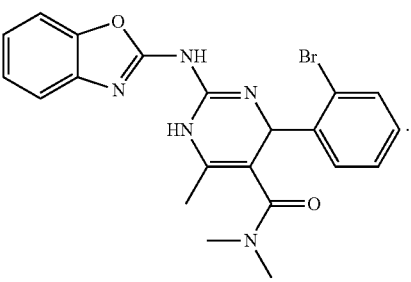
7. The compound or salt of claim 1, wherein the compound is selected from the group consisting of:

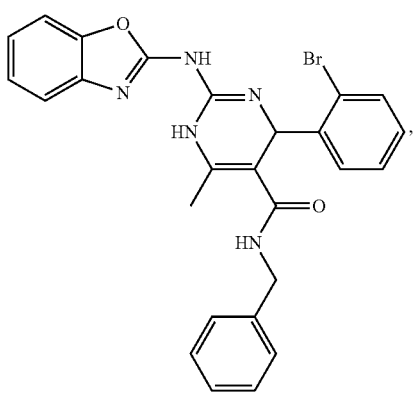
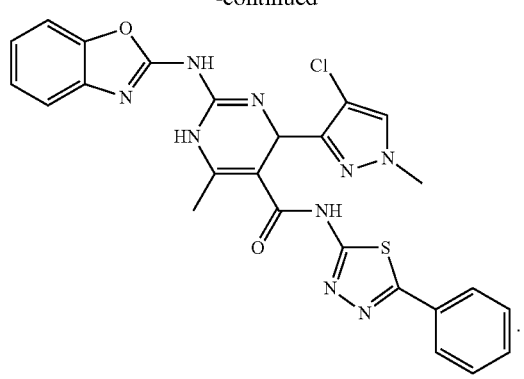
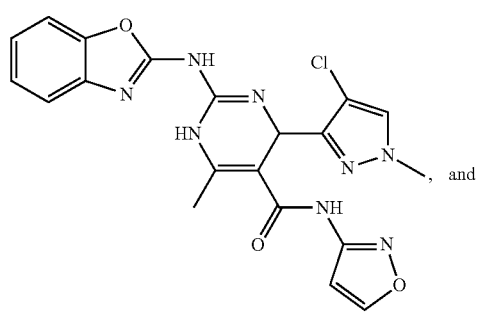
9. The compound or salt of claim 1, wherein the compound is selected from the group consisting of:
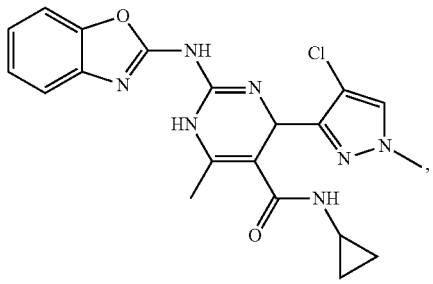
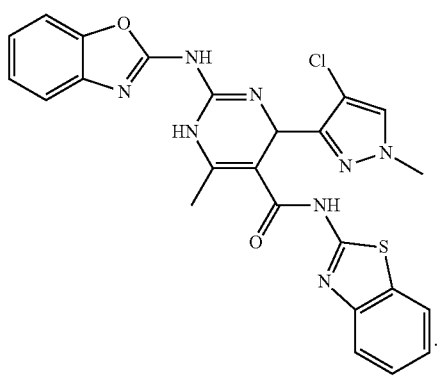
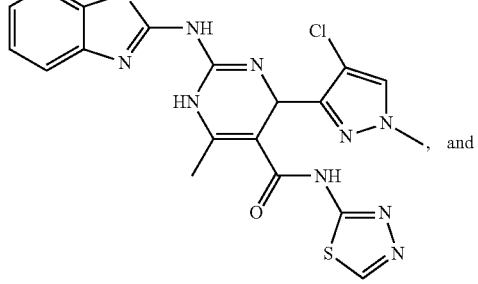
8. The compound or salt of claim 1, wherein the compound is selected from the group consisting of:
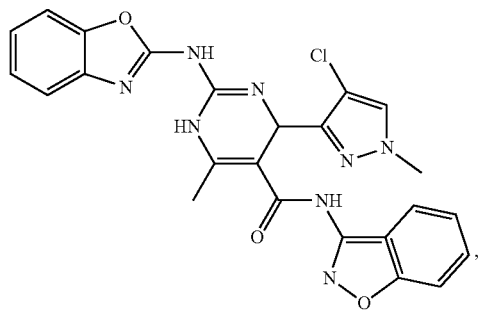
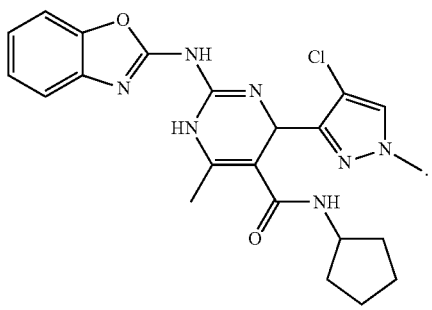
10. The compound or salt of claim 1, wherein the compound is selected from the group consisting of:

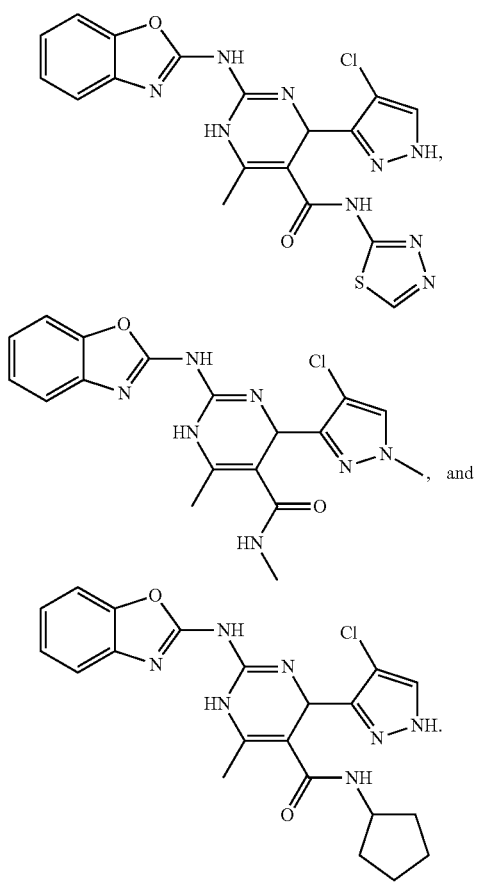
11. The compound or salt of claim 1, wherein the compound is:
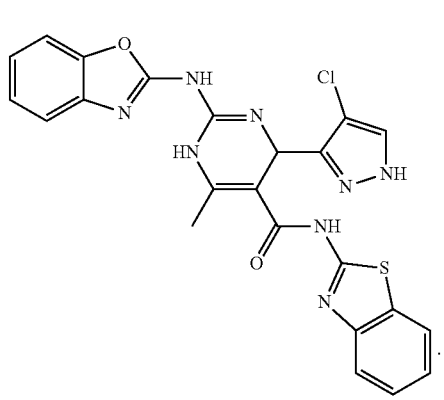 [SMILES: CC1=C(C(=O)Nc2nc3ccccc3s2)C(c2n[nH]cc2Cl)N=C(Nc2nc3ccccc3o2)N1]
12. The compound or salt of claim 1, wherein the compound is selected from the group consisting of:
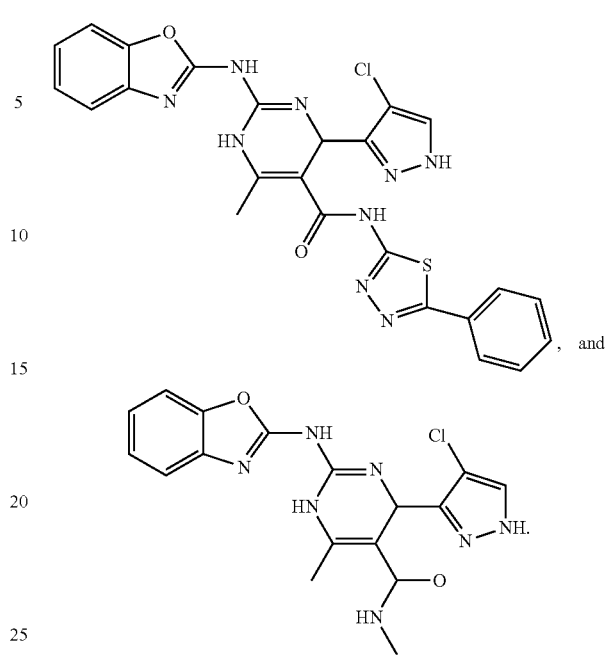
13. The compound or salt of claim 1, wherein the compound is selected from the group consisting of:
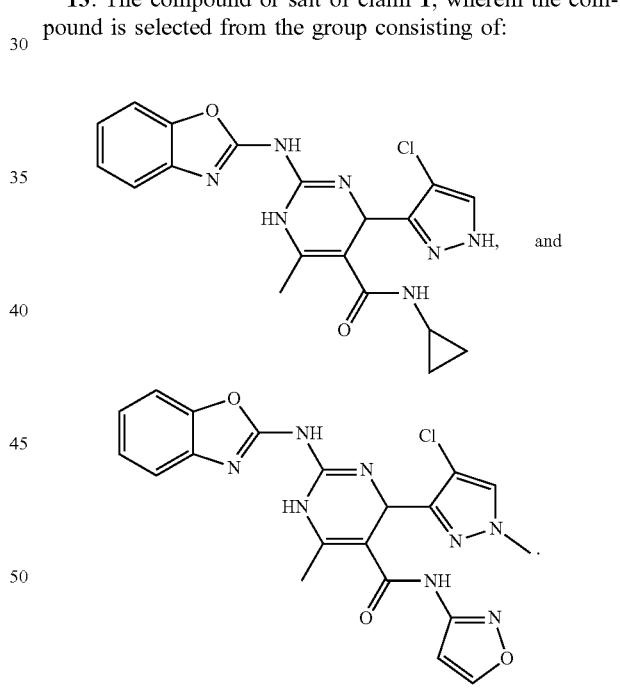
* * * * *

UNITED STATES PATENT AND TRADEMARK OFFICE
CERTIFICATE OF CORRECTION

PATENT NO. : 9,447,087 B2  
APPLICATION NO. : 14/346400  
DATED : September 20, 2016  
INVENTOR(S) : Boxer et al.

Page 1 of 1

It is certified that error appears in the above-identified patent and that said Letters Patent is hereby corrected as shown below:

On the Title Page

(73) Assignee should read:
THE UNITED STATES OF AMERICA, AS REPRESENTED BY THE SECRETARY, DEPARTMENT OF HEALTH AND HUMAN SERVICES OFFICE OF TECHNOLOGY TRANSFER, NATIONAL INSTITUTES OF HEALTH,
Bethesda, Maryland (US)
UNIVERSITY OF UTAH RESEARCH FOUNDATION,
Salt Lake City, UT (US)

Signed and Sealed this
Twenty-eighth Day of August, 2018

Andrei Iancu
*Director of the United States Patent and Trademark Office*